(12) United States Patent
Stephan

(10) Patent No.: US 8,702,291 B2
(45) Date of Patent: Apr. 22, 2014

(54) ILLUMINATABLE APPARATUS AND METHOD OF MANUFACTURING SAME

(76) Inventor: John Stephan, Troy, MI (US)

(*) Notice: Subject to any disclaimer, the term of this patent is extended or adjusted under 35 U.S.C. 154(b) by 365 days.

(21) Appl. No.: 12/984,273

(22) Filed: Jan. 4, 2011

(65) Prior Publication Data

US 2011/0176326 A1    Jul. 21, 2011

Related U.S. Application Data

(60) Provisional application No. 61/350,620, filed on Jun. 2, 2010, provisional application No. 61/305,050, filed on Feb. 16, 2010, provisional application No. 61/292,075, filed on Jan. 4, 2010.

(51) Int. Cl.
  *F21V 7/04*    (2006.01)
(52) U.S. Cl.
  USPC ........... 362/553; 362/259; 362/551; 362/552; 362/554; 362/558; 385/54; 385/115; 385/901; 607/89
(58) Field of Classification Search
  USPC ............ 362/103, 108, 217.01, 551–556, 558, 362/570, 572, 259; 385/54, 115, 116, 120, 385/901; 607/89
  See application file for complete search history.

(56) References Cited

U.S. PATENT DOCUMENTS

| | | | |
|---|---|---|---|
| 4,234,907 A | 11/1980 | Daniel | |
| 4,907,132 A | 3/1990 | Parker | |
| 5,005,108 A | 4/1991 | Pristash et al. | |
| 5,042,900 A | 8/1991 | Parker | |
| 5,092,793 A | 3/1992 | Stephan | |
| 5,136,480 A | 8/1992 | Pristash et al. | |
| 5,424,922 A | 6/1995 | Wise | |
| 5,616,140 A | 4/1997 | Prescott | |
| 6,156,028 A | 12/2000 | Prescott | |
| 6,165,205 A | 12/2000 | Neuberger | |
| 6,201,915 B1 | 3/2001 | Rizkin | |
| 6,290,713 B1 | 9/2001 | Russell | |
| 6,733,187 B2 | 5/2004 | Page et al. | |
| 6,872,220 B2 | 3/2005 | Williams et al. | |
| 6,874,925 B2 | 4/2005 | Page et al. | |
| 7,137,416 B2 | 11/2006 | Brochier et al. | |
| 7,147,653 B2 | 12/2006 | Williams et al. | |
| 7,234,853 B2 | 6/2007 | Givoletti | |
| 7,305,163 B2 | 12/2007 | Williams | |

(Continued)

OTHER PUBLICATIONS

User's Manual Published 2008 Zheng An (Beijing) Medical Equipment Co. Ltd. Manufacturer Zheng An (Beijing) Medical Equipment Co. Ltd. Address: No. 18.KangbaoRoad. IndustrialDevelopmentArea. MiyunTown.Beijing.China.

(Continued)

*Primary Examiner* — Stephen F Husar
*Assistant Examiner* — Meghan Dunwiddie
(74) *Attorney, Agent, or Firm* — Young, Basile, Hanlon & MacFarlane, P.C.

(57) ABSTRACT

An illuminatable apparatus includes a fabric sheet containing fiber optic rods interwoven with fabric threads. The ends of the fiber optic rods are bundled together to form a ferrule which is removably insertable into a holder carrying a light source and a power source. An outer ferrule can be fixed over the sleeve-like ferrule or robust applications. The holder may be removably attached to articles of clothing. The illuminatable fabric sheet can be used as an optical bandage, in a medical cast, in a negative pressure device, or in a bed pad/sheet, or in a therapeutic brace support.

15 Claims, 29 Drawing Sheets

(56) References Cited

U.S. PATENT DOCUMENTS

| | | |
|---|---|---|
| 7,331,983 B2 | 2/2008 | Neuberger |
| 7,479,664 B2 | 1/2009 | Williams |
| 7,686,839 B2 | 3/2010 | Parker |
| 2006/0087864 A1 | 4/2006 | Peng et al. |
| 2008/0172112 A1 | 7/2008 | Gourgouliatos et al. |
| 2008/0198578 A1 | 8/2008 | Finn |
| 2009/0012586 A1 | 1/2009 | Kepecs |
| 2009/0024190 A1 | 1/2009 | Irvine |
| 2009/0054957 A1 | 2/2009 | Shanbaky |
| 2009/0088822 A1 | 4/2009 | Pruitt et al. |
| 2009/0099628 A1 | 4/2009 | Williams |
| 2009/0112296 A1 | 4/2009 | Weisbert et al. |
| 2009/0124958 A1 | 5/2009 | Ll et al. |
| 2009/0132012 A1 | 5/2009 | Shanks |
| 2009/0216301 A1 | 8/2009 | Streeter et al. |
| 2010/0241196 A1 | 9/2010 | Meyer |

OTHER PUBLICATIONS

LumiGram Light for Style Copyright 2006-2008 LumiGram.

Fiber Optics in Textile Published Jan. 5-7, 2005.

Chinese Publication No. 97104484.8 published May 6, 1998.

International Search Report for PCTUS2011020118 completed Feb. 24, 2011 and mailed Mar. 3, 2011.

Written Opinion of the International Searching Authority for PCTUS2011020118 completed Feb. 24, 2011 and mailed Mar. 3, 2011.

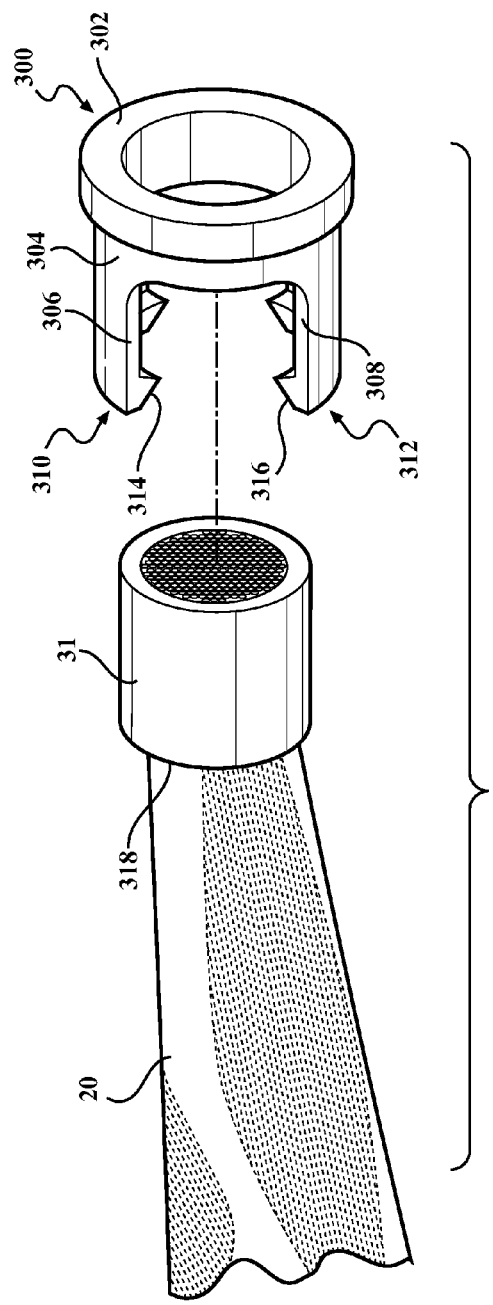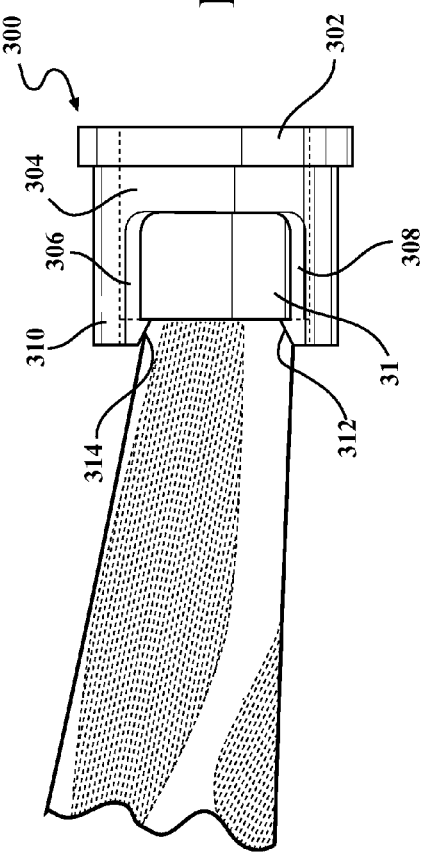

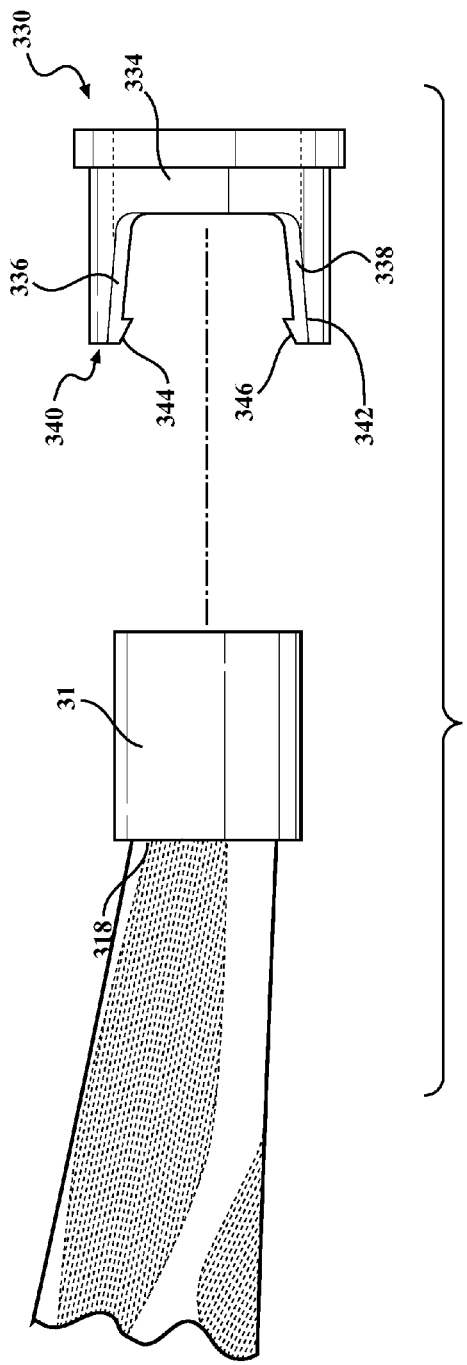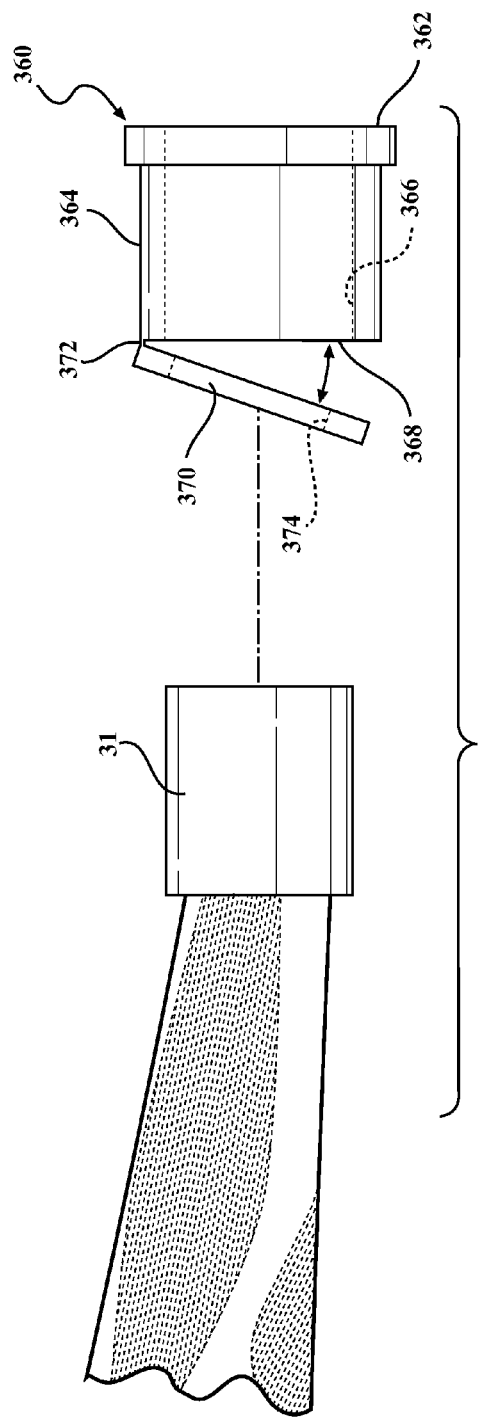

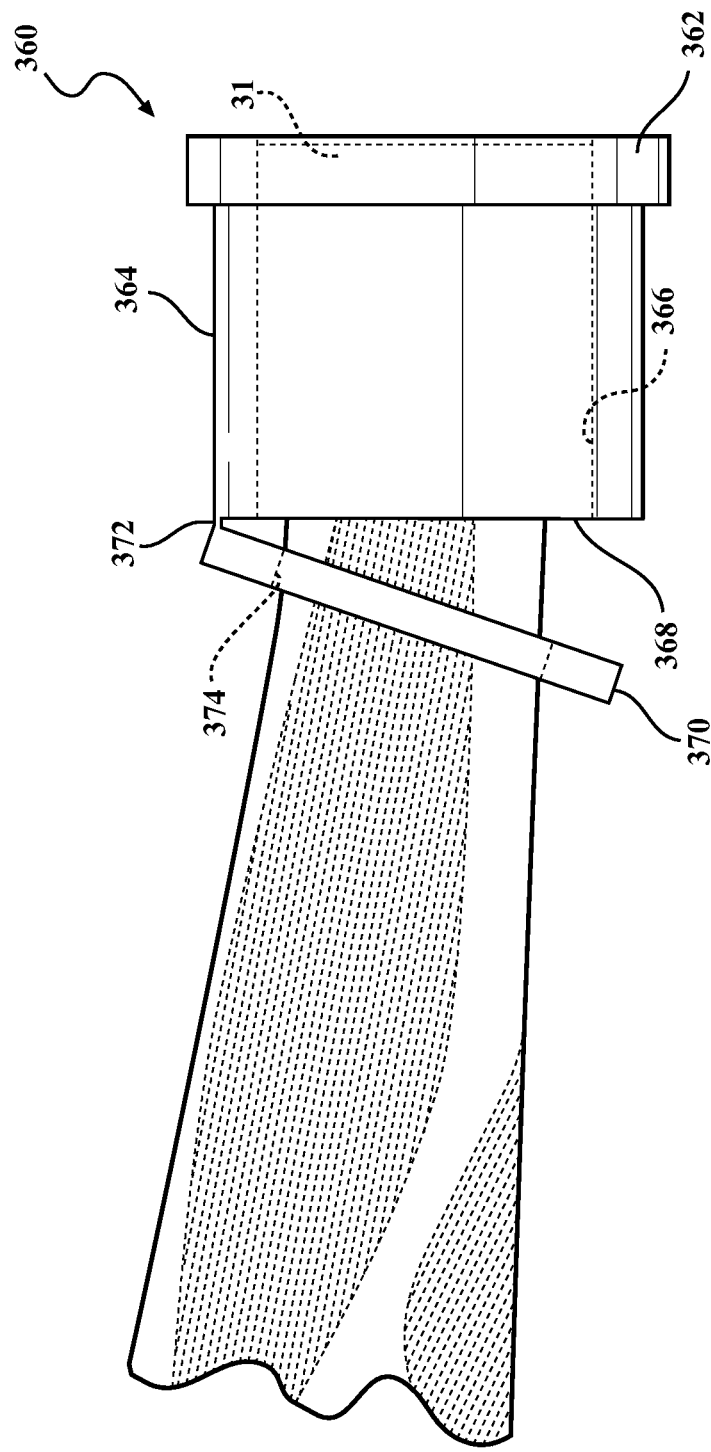

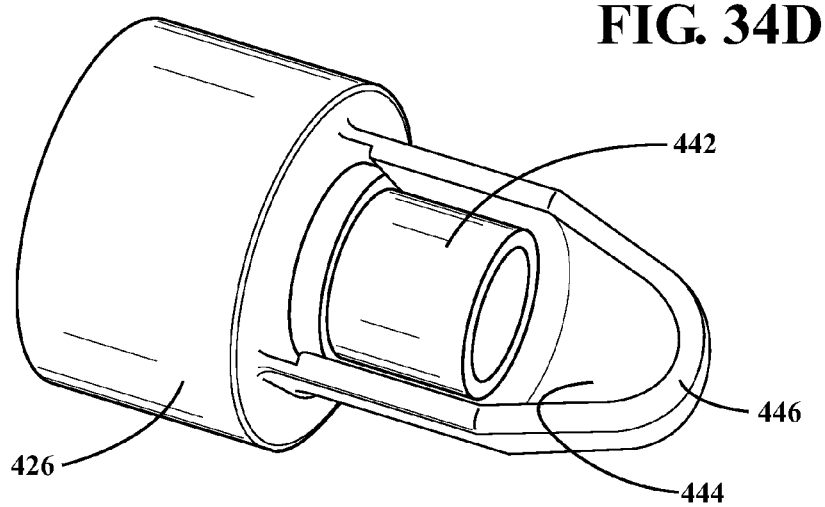
FIG. 34D
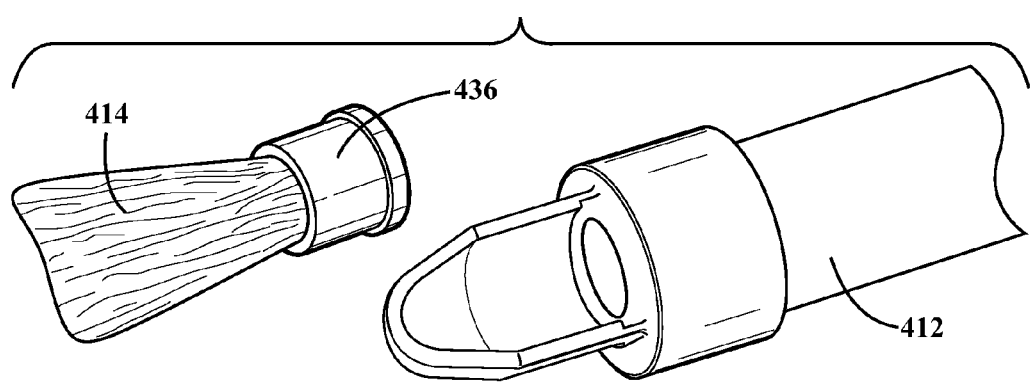
FIG. 34E
FIG. 34F
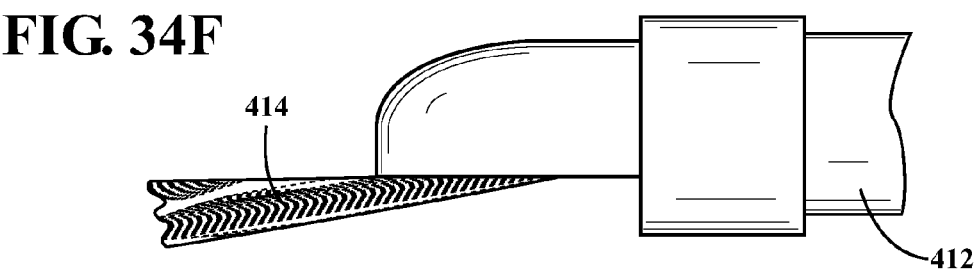

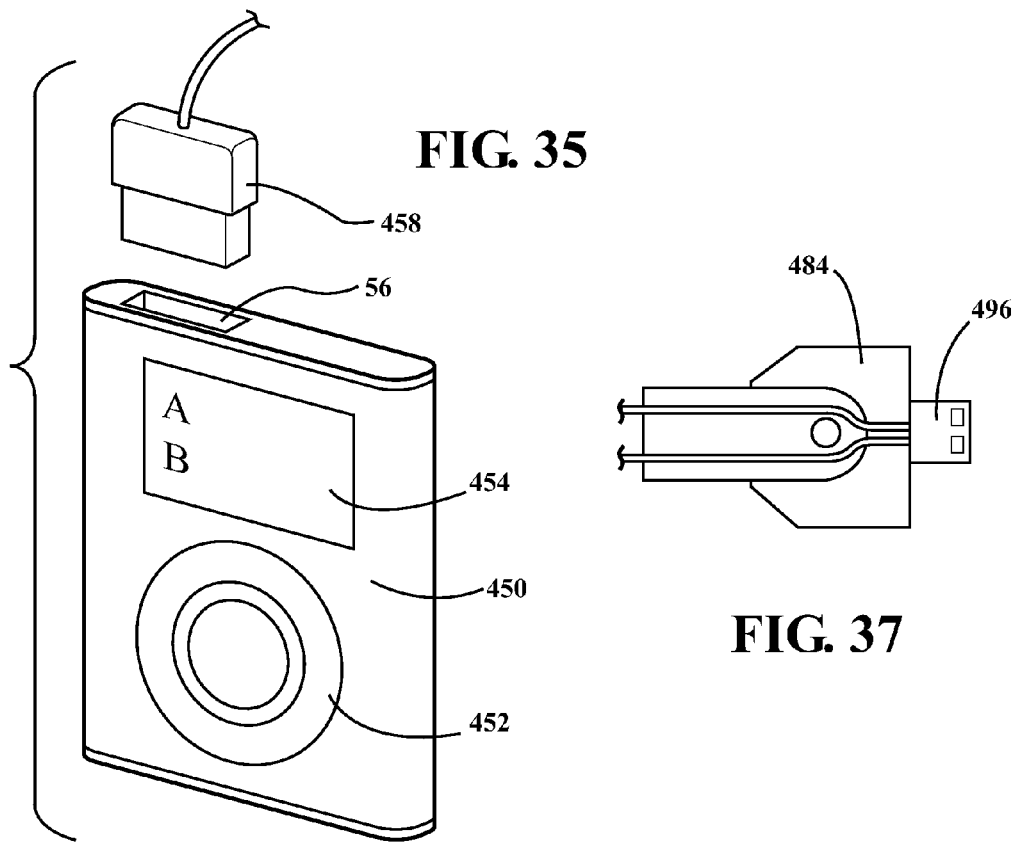
FIG. 35
FIG. 37
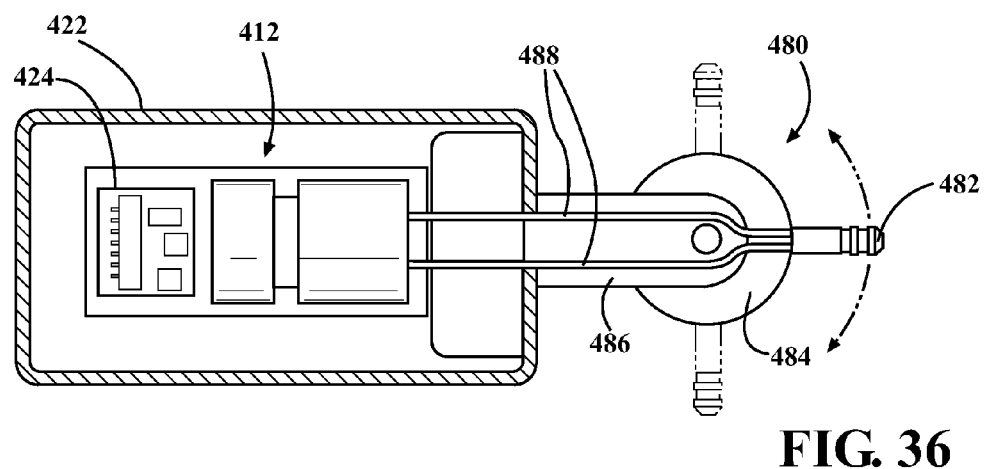
FIG. 36

ILLUMINATABLE APPARATUS AND METHOD OF MANUFACTURING SAME

CROSS REFERENCE TO CO-PENDING APPLICATIONS

This application claims priority benefit to the filing date of U.S. Provisional Patent Application Ser. No. 61/292,075, filed Jan. 4, 2010 for "Light Therapy Apparatus", and U.S. Provisional Patent Application Ser. No. 61/305,050, filed Feb. 16, 2010 for "Light Therapy Apparatus Including Optical Bandage With Optional Sensor", and U.S. Provisional Patent Application Ser. No. 61/350,620, filed Jun. 2, 2010 for "Illuminated Fabric Articles", the entire contents of each which are incorporated herein in its entirety.

BACKGROUND

Light therapy devices using light emitting diodes and lasers diodes have been used for therapeutic application to humans for the treatment of various medical and physical disorders.

Fabric or textile products incorporating illuminated fiber optic fibers or rods interwoven by fabric threads and connectible to a light source have also been devised. Such illuminated fabrics have been incorporated into bandages for medical treatment as well as in articles of clothing for aesthetic purposes.

In each application of the illuminated fabric products, one end of the optical fibers are bundled together and attached to a connector which provides an interface to a light source.

It would be desirable to provide improvements in connectors for optical fiber products. It would also be desirable to provide an illuminatable article using illuminatable fabric and a laser light source in which the interface between the laser light source and the optical fabric enables a user to connect the light source to the fabric without the use of a skilled medical technician.

SUMMARY

An illuminatable article in the form of an optical fabric sheet including fiber optic rods extending in one direction interwoven with fabric threads and a plastic sleeve or ferrule tightly compacting one end of the fiber optic rods into a bundle with the ends of the fiber optic rods in the bundle exposed.

A holder carries a light source and an electrical power source for powering the light source. At least one mount is carried by the holder for fixedly receiving the plastic sleeve on the bundled end of the fiber optic rods of the fabric sheet and disposing the exposed ends of the fiber optic rods in a fixed dimensional relationship with the light source in the holder.

The light source can be at least one light emitting diode.

The plastic sleeve is adhesively fixed to the bundled end of the fiber optic rods.

The adhesive can be carried internally within a heat shrinkable tube to fix the heat shrinkable tube to the bundle end of fiber optic rods.

An outer ferrule has a through bore extending between opposed first and second ends. The outer ferrule has at least one bendable leg extending to the second end, and projection carried by the bendable leg snapping over one end of the plastic sleeve to couple the outer ferrule to the plastic sleeve.

In another aspect, the outer ferrule has a through bore extended between opposed first and second ends, a panel hingedly coupled at one end to the outer ferrule, and an aperture formed in the panel sized to receive the plastic sleeve on the bundled end of the fiber optic rods for insertion of the sleeve and the bundled end of the fiber optic rods into the bore in the outer ferrule only when the aperture in the hinged panel is concentrically aligned with the bore in the outer ferrule.

The holder includes power supply compartment removably receiving at least one battery, and connections carried by the holder for connecting electric power from the battery to at least one light source carried in the holder. A receiver in the holder removably receives an outer ferrule mounted on the bundled end of the fiber optic rods in the fabric product. A removable cover is attachable to the holder and coacts with the receiver in the holder for removably securing the outer ferrule to the holder. An on/off switch is accessible through the holder and coupled to the electric power connections between the power source and the at least one light source in the holder.

In another aspect, a rigid outer ferrule has a through bore extending between opposed first and second ends. The receiver includes a panel hingedly coupled at one end to the outer ferrule and an aperture formed in the panel sized to receive the plastic sleeve on the bundled end of the fiber optic rods for insertion of the sleeve and the bundled end of the fiber optic rods into the bore in the outer ferrule only when the aperture in the hinged panel is concentrically aligned with the bore in the outer ferrule.

A method of forming an interface at one end of a fabric product including fiber optic rods interwoven with fabric threads includes the steps of forming one end of the fiber optic rods into a tightly compacted bundle, temporarily holding the ends of the fiber optic rod in the bundle, inserting a plastic sleeve over the bundled end of the fiber optic rods, and fixing the plastic sleeve to the bundled end of the fiber optic rods.

After the plastic sleeve is affixed to the bundled end of the fiber optic rods, the exposed ends of the fiber optic rods in the bundle are cut to form a common plane for all of the ends of the fiber optic rods in the bundle.

The step of temporarily holding the fiber optic rods in a bundle includes winding adhesive tape around the bundled ends of the fiber optic rods.

The step of temporarily holding the fiber optic rods in a bundle alternately includes winding a thread around the bundled end of the fiber optic rods.

A kit for forming an illuminated article includes a holder carrying a light source and an electric power source, a length of illuminatable fabric including fiber optic rods interwoven with fabric thread, one end of the fiber optic rods arranged in a tightly bundled compact form and a ferrule fixedly mountable over the bundled end of the fiber optic rods and adapted for removable insertion into the holder.

The illuminated article can be a negative pressure device formed of at least one layer of porous material adapted to surround a wound on a patient and at least one layer of illuminatable fabric layered with the at least one layer of the porous material.

In one aspect, a body fixedly carries the holder. The body is an ornamental body. A clip carried by the ornamental body removably mounts the body to a clothing article.

In one aspect the optical fabric sheet is arranged in a compact overlapped arranged in multiple overlapped layers, for mounting to an article of clothing.

In another aspect, the illuminatable article is a light therapy apparatus including a laser for emitting at least one laser beam of laser light having a light intensity greater than a class I laser rating, a power supply operatively connected to the laser means, a control, operatively connected to the power supply and the laser, for controlling the laser to emit laser light for a predetermined period of time, and means, optically coupled to the laser, for diffusing the intensity of the laser light generated by the laser when applied to a patient to an intensity no greater than the output of a class I rated laser.

The laser is one of a class III and a class IV rated laser.

The diffusing means contains fiber optic fibers optically coupled at one end to the laser means, with fiber optic fibers formed in an enlarged pad for diffusing the laser light over an area.

The light therapy apparatus includes a circuit element activating the laser for a predetermined period of time and predetermined period of times over a longer predetermined time interval.

The light therapy apparatus has a control including a first frequency output activating the laser means at a first duty cycle over a predetermined time interval.

The control can provide a plurality of distinct frequency outputs.

The first frequency output duty cycle and the predetermined time interval defines a tune.

The control is capable of outputting a plurality of selectable distinct audio tunes for therapeutic purposes.

The illuminatable article is an optical bandage including a light source for emitting light energy, a power supply operatively coupled to the light source, a control, operatively coupled to the power supply and the light source, for controlling the light source to emit light energy for predetermined period of time, and light applicator optically coupled to the light source for diffusing light from the light source over an area; and at least one layer of a biologically clean material coupled to the light applicator.

In one aspect, the layer comprises a single material layer. The layer may also be an envelope substantially surrounding the light applicator.

In one aspect, the light applicator and the material layer are interwoven into a single layer.

In another aspect of the optical bandage, a plurality of light applicator rods are coupled to a sensor for directing reflected light from the article on which the optical bandage is mounted to the sensor.

In another aspect, the illuminated article is an optical cast of at least one layer of an interwoven light applicator and cloth material, the ends of the light applicator extending outward from the first layer enjoined in a ferrule adapted for connection to a light source, a shock absorbent material layer disposed about the first layer; and an outer hardened material layer.

BRIEF DESCRIPTION OF THE DRAWING

The various features, advantages, and other uses of the present illuminatable apparatus will become more apparent by referring to the following detailed description and drawing in which:

FIG. 7 is an exploded side perspective view of another aspect of a ferrule;

FIG. 8 is a side elevational view showing the assembled ferrule of FIG. 7 on the bundled end of an optical fabric;

FIG. 9 is an exploded side elevational view of another aspect of a ferrule;

FIG. 10 is an exploded side elevational view of another aspect of a ferrule;

FIG. 11 is an side elevational view of the ferrule of FIG. 10 assembled on the bundled end of an optical fabric;

FIG. 34D is a perspective view of a deflector cap for the light source shown in FIG. 34B;

FIGS. 34E and 34F are perspective views showing the attachment of the ferrule at one end of the optical fabric to the cap shown in FIG. 34D mounted on one end of the light housing;

FIG. 35 is a perspective view of another aspect of a light therapy apparatus;

FIG. 36 is a partially broken away, plan view of another aspect of a light generating portion of a light therapy apparatus including a swivel connector;

FIG. 37 is a side elevational view of an alternate swivel connector;

DETAILED DESCRIPTION

Referring now to FIGS. 1A-1G, there is depicted a textile or fabric product 20 with illuminated optical fibers 22 interwoven with cross woven fabric threads 24. Such a textile product is disclosed in the U.S. Pat. No. 7,234,853 and manufactured by Luminex, S.p.A. of Prato, Italy.

Figure 2:
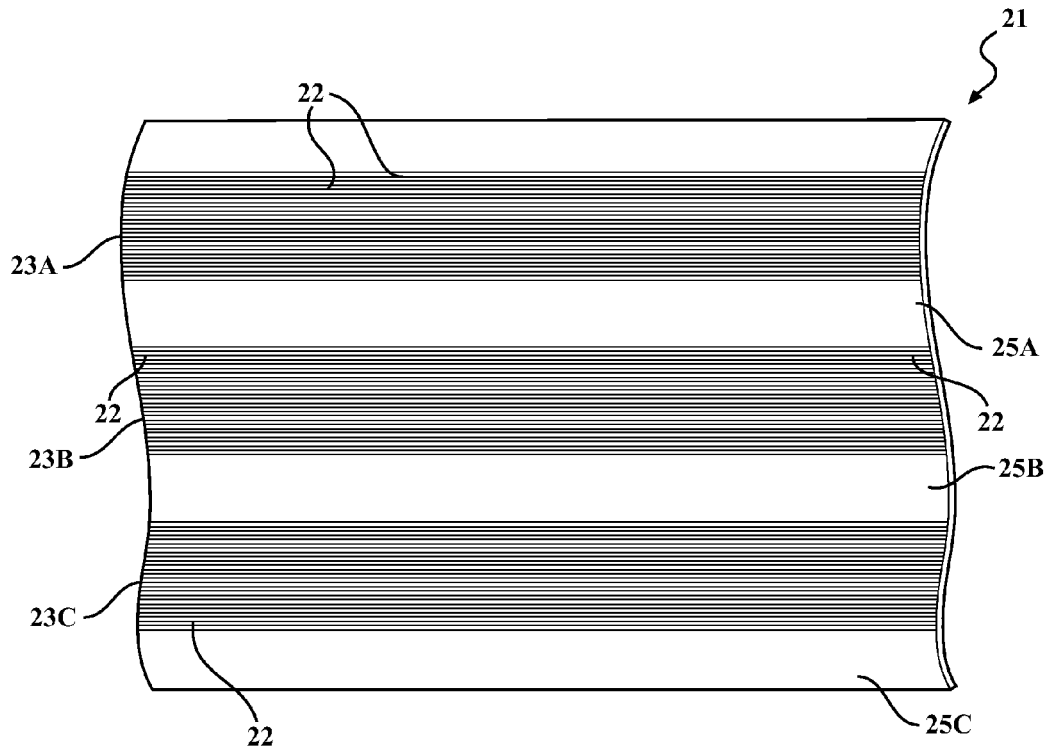
FIG. 2 is a perspective view of another aspect of an optical fabric.
Figure 3:
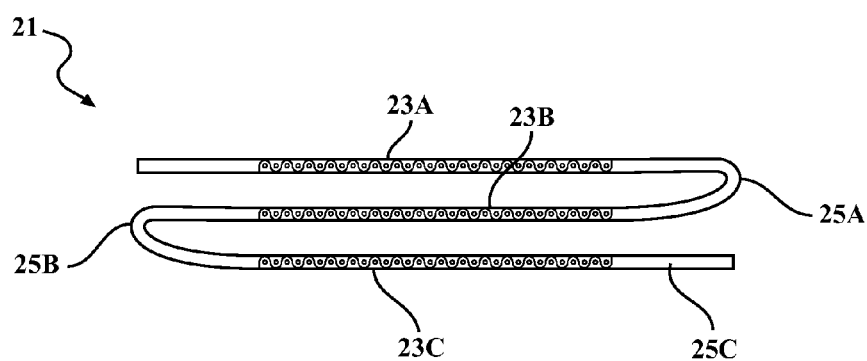
FIG. 3 is an end elevational view showing the overlapping of the optical fabric depicted in FIG. 2.

As shown in FIGS. 2 and 3, the textile or fabric product 21 may also be is formed of a continuous panel of laterally and longitudinally extending, interwoven fabric threads. A plurality of spaced longitudinally extending rows 23A, 23B and 23C, for example, of optical fibers 22 are interwoven with the fabric threads in the fabric product 21. The spacing between each row 23A, 23B and 23C of optical fibers 22 may have any dimension. However, as shown in FIG. 2, the areas of the fabric product 21 between the rows 23A, 23B and 23C of optical fibers 22 may have a narrower width than the width of the rows 23A, 23B, and 23C to form narrow bands 25A, 25B, and 25C between the spaced rows of 23A, 23B and 23C of optical fibers. This arrangement of rows of optical fibers spaced apart by completely fabric rows without optical fibers allows the fabric product 21 to be folded over on itself one or more times, shown in FIG. 3. This arranges the rows 23A, 23B and 23C of optical fibers 22 in an overlaid arrangement to which increases the intensity or brightness of the light emitted by the optical fibers 22.

Figure 1A:
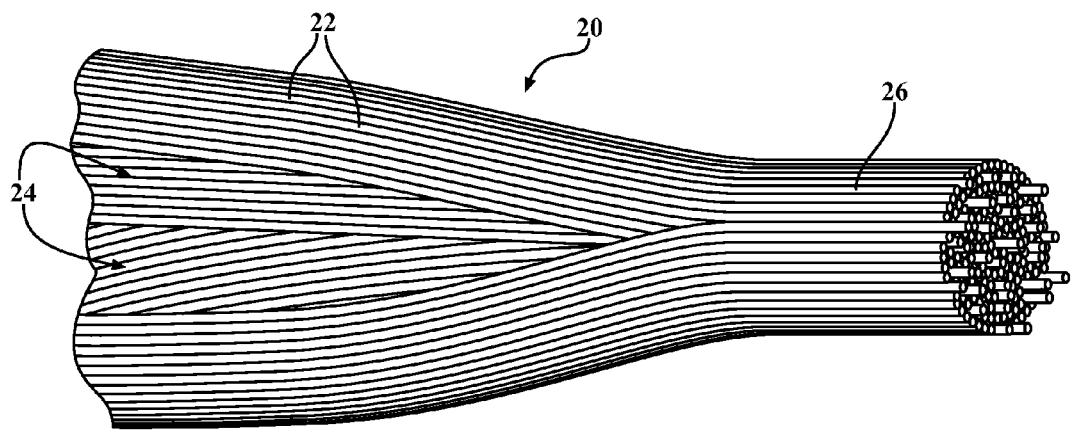
FIGS. 1A-1G are pictorial representations of the process steps of one aspect of forming a ferrule at a bundled end of optical fibers in an optical fabric.

It is also possible in either of the fabric products 20 or 21 shown in FIGS. 1A and 3 to apply abrasions or otherwise roughen up the exterior surface of the optical fibers 22. The area of roughened surface area of the optical fibers 22 may extend along the entire length of the optical fibers 22 or only in certain desired areas. The roughened area creates scratches in the surface of the optical fibers 22 which allows light to escape from the interior of the optical fibers 22. This causes light to be emitted over a larger portion of the fabric product 20 or 21 to again increase light intensity.

The roughened surface or scratches may be formed by any suitable tool or process, such as by rubbing a nail file or emery board over the surface of the optical fibers 22, either prior to weaving with the fabric threads or after the optical fibers 22 have been woven with the fabric threads into the optical product 20 or 21.

The ends of the optical fibers 22 and the threads 24 along one edge of a fabric sheet 20 are bound together into a tightly packed circular bundle 26 at one end of the fabric 20 and held in place by means of a ferrule, not shown, which is press fit over the bundled end 26. The ferrule enables the bundled end 26 of the optical fibers 22 to be inserted into a connector in close dimensional relationship with a light source, such as an LED.

The unique process for forming the bundled end 26 of the optical fibers 22 in the fabric 20 into a spree includes the steps of:

1. Grasping and bundling one end of the optical fibers 22 and the cross threads 24 in the fabric 20 into the closely packed bundle 26 shown in FIG. 1A.

Figure 1B:
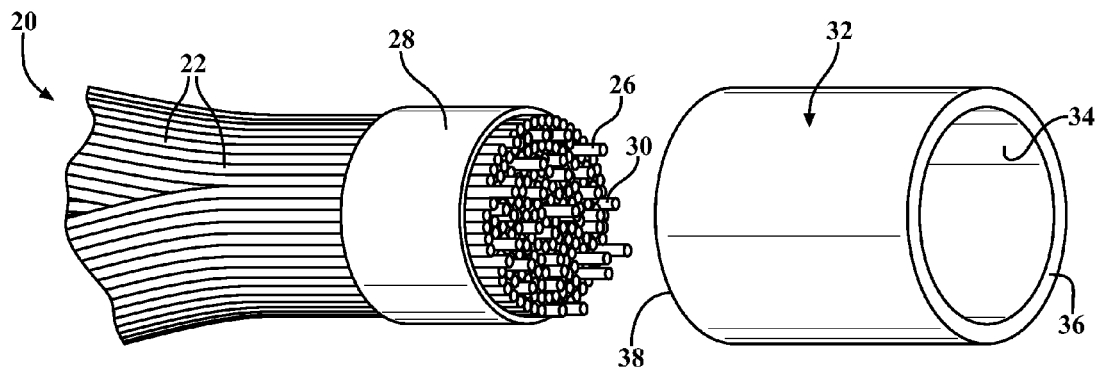

2. The bundle 26 of the optical fibers 22 can optionally be temporarily held in place by means of a thin strip of adhesive tape 28 as shown in FIG. 1B. The tape 28 is tightly wound around an intermediate portion of the bundle 26 to form a spree while allowing the ends 30 of the optical fibers 22 and the cross threads 24 to extend outward from one edge of the tape 28.

It should be noted that the fabric threads can be stripped out of the end so that the bundled end 2 contain only optic fibers 22. This enables the end 26 to have a diameter of 5-6 mm for maximum reception of light from the light source.

Figure 1C:
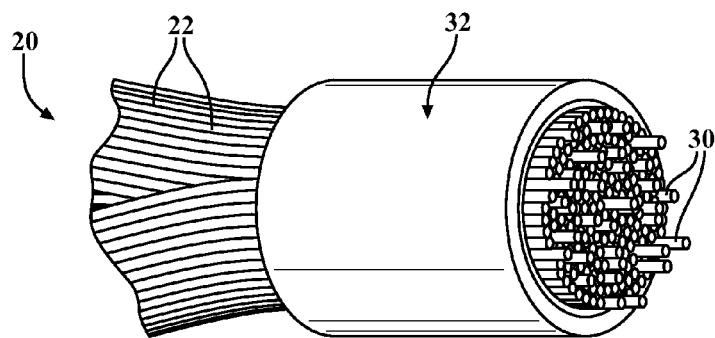

3. As also shown in FIGS. 1B and 1C, a tubular sleeve or aglet 32 with an outer diameter commensurate with the outer diameter of the bundled ends 26 of the optical fibers 22 is inserted over the bundled end 26. The sleeve 32 can have an outer diameter of 5 mm, for example only. The sleeve 32 has a hollow throughbore 34 extending from a first end 36 to an opposed second end 38.

4. As shown in FIG. 1C, the sleeve 32 is inserted over the tape layer 28 and the bundled end 26 of the optical fibers 22. In the position of the sleeve 32 shown in FIG. 1C, the sleeve 32 closely surrounds the outer diameter of the bundled ends 26 of the optical fibers 22.

Figure 1D:
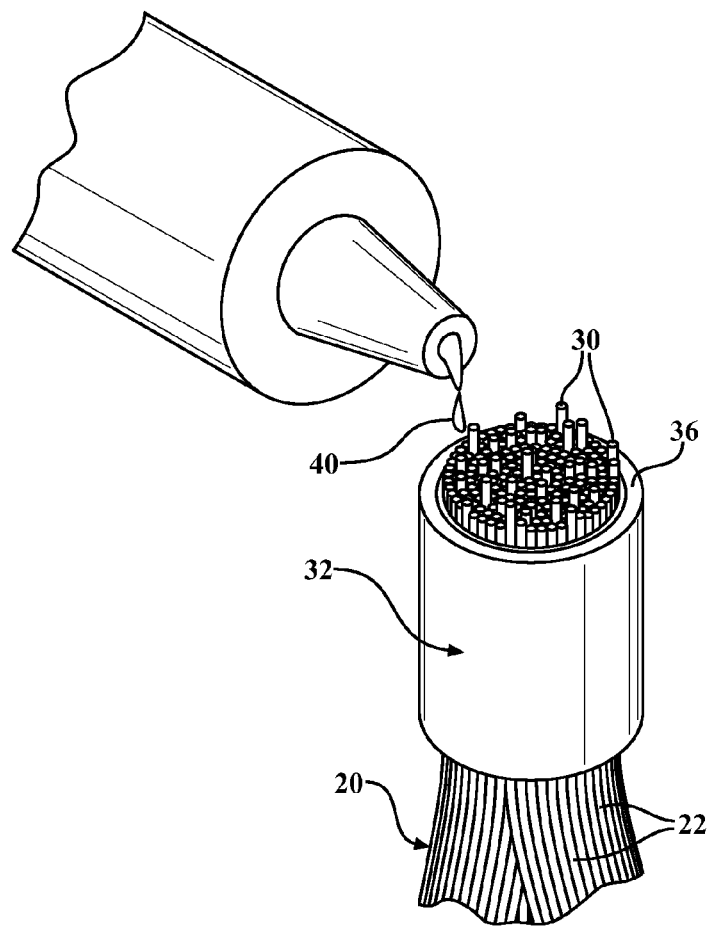

5. Next, as shown in FIG. 1D, an adhesive 40 is applied to the free ends 30 of the optical fibers 22 and into the voids between the optical fibers 22 within the bundled end 26 inside of the sleeve 32. The adhesive 40, which can be an epoxy, for example, fills all of the voids between the individual optical fibers 22 within the sleeve 32 to center the optical fibers 22 within the sleeve 32. The adhesive 40 when cured maintains the ends of the optical fibers 22 in non-movable position within the sleeve 32.

The adhesive 40 can also be an adhesive which can be cured by UV radiation to a soft pliable state while still holding the sleeve 32 on the bundle 26 of the fibers 22.

The adhesive may also be a wicking type of adhesive since the transverse fabric fibers 24 are made of absorptive material. This allows the cross threads 24 to wick the adhesive into the interior of the cross threads 24 due to their porosity. This enables the bundled end 26 to be formed not as a solid fill, like prior connectors using a ferrule, but rather as a porous, fixed, rigid ferrule or aglet.

Figure 1E:
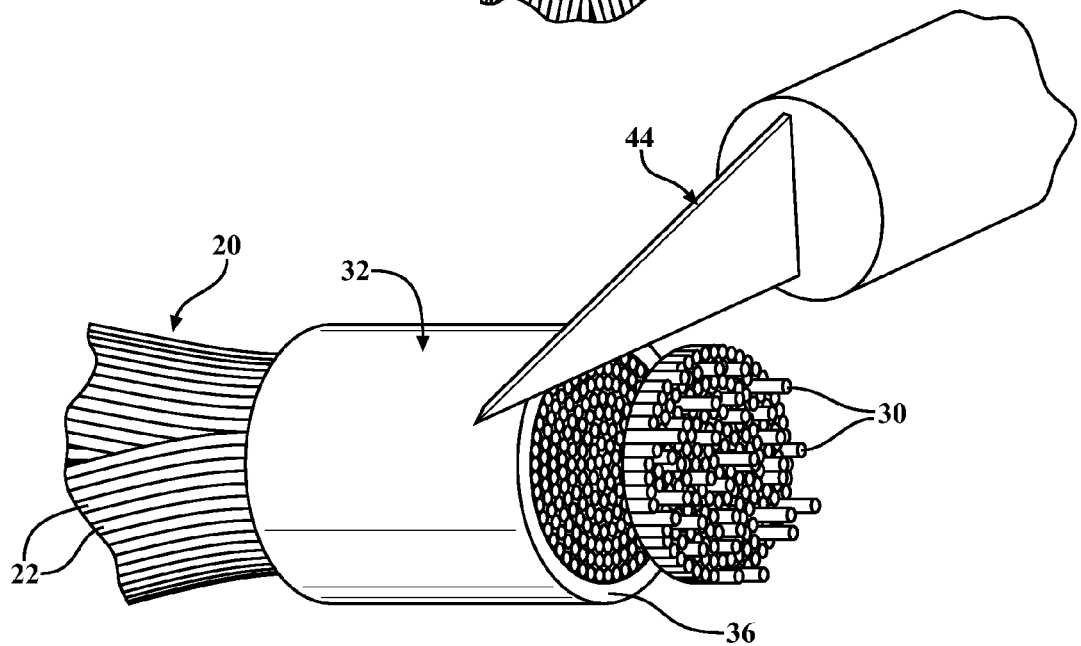

6. In a next step, the free ends 30 of the optical fibers 22 extending beyond the first end 36 of the sleeve 32 are removed. A suitable cutting instrument 44, as shown in FIG. 1E, is used to cut or remove the free ends 30 of the optical fibers 22 which extend beyond the first end 36 of the sleeve 32. A PVC pipe cutter 44 is shown in FIG. 1E as an example of a cutting instrument. Alternately, the free ends 30 of the optical fibers 22 may be removed by means of grinding or other material removal processes.

Figure 1F:
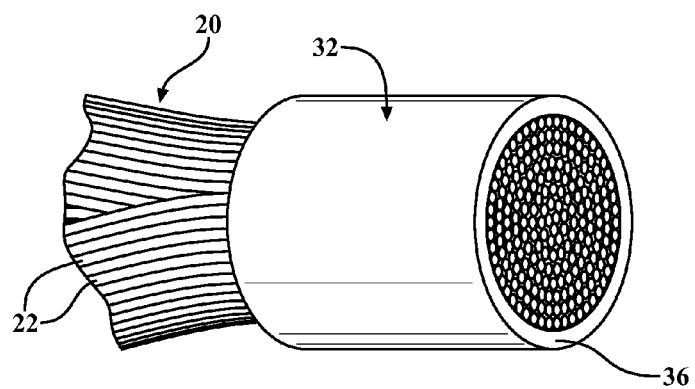
Figure 1G:
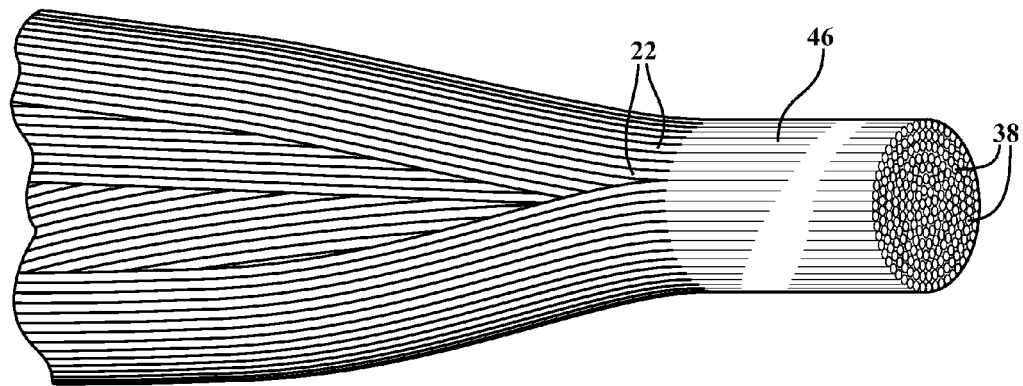

Depending upon the material used as the adhesive 40 and the sleeve 32, the sleeve 32 can be adhered by the adhesive to the fibers 22 or not joined to the fibers In the case of the sleeve 32 made of polypropylene and similar materials, and the adhesive 40 being made of epoxy, the propylene sleeve 32 will not be adhered by the adhesive 42 to the outer surface of the bundled end 26 of the optical fibers 22. The sleeve 32 can be removed from the bundled end 26, as shown in FIG. 1G. For other sleeve and adhesive materials 40, the adhesive 40 may securely bind the sleeve 32 to the bundled ends 46 of the optical fibers 22 as shown in FIG. 1F.

After removal, the cut ends 38 of the optical fibers 22 are perpendicular to the axial centerline of each fiber 22 for maximum light receptivity.

Figure 4A:
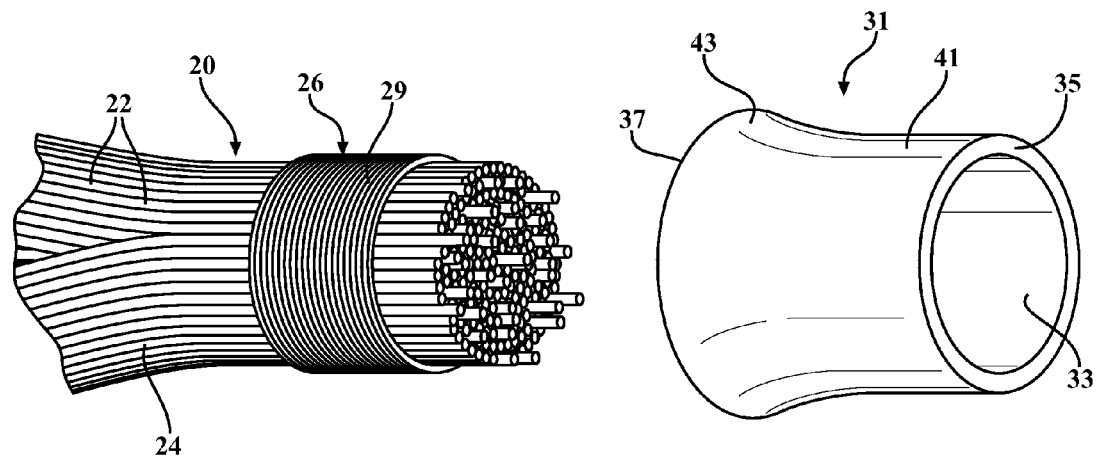
FIGS. 4A and 4B are pictorial representations of the process steps of another aspect for forming a ferrule.
Figure 4B:
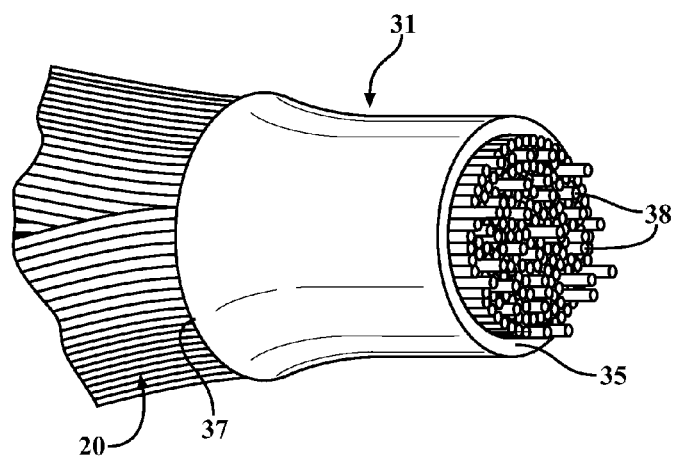

As shown in FIGS. 4A and 4B, an alternate method of forming the ferrule is depicted. The ends of the optical fibers 22 are again grasped and formed into a bundle 26 as shown in FIG. 4A. The bundle 26 is covered with a wound thread 29 as shown in FIG. 4A. The thread 29 can be wound, for example, from left to right in the orientation shown in FIGS. 4A and 4B and cut at the end of the optical fibers 22. With the user holding both cut ends of the wound thread 26 tightly about the bundle 26, a tubular sleeve or ferrule 31 formed of a heat shrinkable material is slid over the thread 29 and the tightly bound bundle 26 of optical fibers 22. With the sleeve 31 disposed over the thread bound bundle 26, the thread 29 which has been held in place over the bundle 26 by the user, is released and can be unwound from the bundle 26 before the full length of the sleeve 31 is slid over the bundle 26.

The ferrule 31 is in the form of a hollow tube having a through bore 33 extending from a first end 35 to an opposed second 37. The ferrule 31 has a constant diameter portion 41 extending from the first end 35 and smoothly tapers outward to an enlarged portion 43 which terminates at the second end 37. The flared end portion 43 forms the opening at the second end 37 of the ferrule 31 with a larger diameter than the nominal diameter of the bundle 26 of the optical fibers 22. This allows easy insertion of the flared end portion 43 of the ferrule 31 over the bundled end 26 as shown in FIGS. 4A and 4B.

A heat source, such as the heat gun, is used to apply heat to the ferrule 31 to shrink the diameter of the ferrule 31 to a smaller diameter tightly and securely binding the loose ends of the optical fibers 22 into a compact, fixed circular binding diameter end.

An adhesive, such as one or two drops of a soft pliable, UV curable cyanoacrylic adhesive can be applied at one end of the sleeve 31 at the joint between the end of the sleeve 31 and the fabric 20 as the fabric 20 exits the end of the sleeve 31. The adhesive securely fixes the sleeve 31 on the bundled end 26 of the optical fibers 22 in the fabric 20.

The heat shrunk tube 31 can function by itself by a ferrule for light duty applications where the ferrule 31, once mounted in a suitable holder, as described hereafter, is not subject to excessive removal and insertion operations. A small amount of a heat activated adhesive can be applied to an inner surface of the tube 31 to join the tube 31 to the sleeve 31 when heat is applied to the tube 31.

Figure 5:
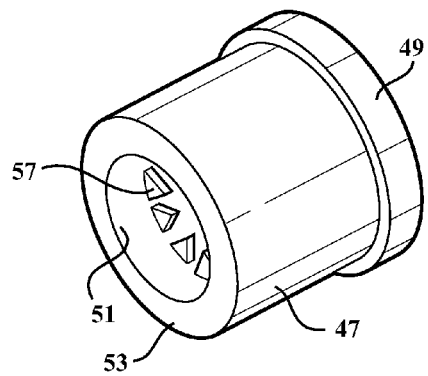
FIG. 5 is an enlarged perspective view of one aspect of a ferrule.
Figure 6:
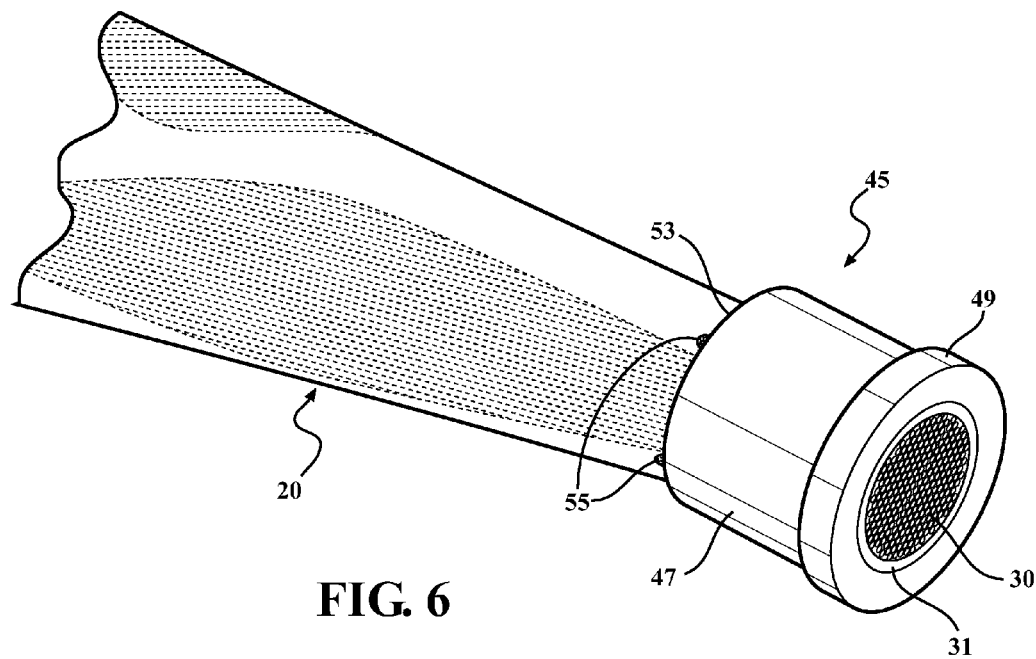
FIG. 6 is a perspective view showing another step in the process of mounting the ferrule depicted in FIG. 5 on a bundled end of an optical fabric.

In more rigorous applications where the bundled ends 26 of the optical fibers 22 are in the fabric product 20 are subject to repeated removals and reinsertions into a light source holder, an outer ferrule 45, shown in FIGS. 5 and 6, may be employed.

The ferrule 45 formed of a rigid plastic and having a constant diameter tubular sleeve portion 47 and an enlarged diameter end flange 49, both of which surround an internal bore 51, is inserted over the heat shrunk sleeve tube 31 and secured in place by one or more drops of adhesive 55, such as super glue, applied between the end 53 of the tubular sleeve 47 opposite from the enlarged flange 49 and the outer surface of the optical fibers 22.

As shown in FIG. 5, the ferrule 45 includes a plurality of internal teeth or projections 57. The projections 57 can extend around the entire or cut spaced intervals of the inner diameter of the tubular sleeve 47 and taper to a pointed end which can be disposed at an acute angle with respect to the interior surface of the tubular sleeve 47 with respect to the first end of the tubular sleeve 47 at the enlarged flange 49. During insertion of the bundled ends of the bundle 26 of the ends 30 of optical fibers 22 in the fabric product 20 through the end 53 into the internal bore 51 in the tubular sleeve 47, the ferrule 31 surrounding the bundled ends of the optical fibers 22 slides easily over the projections 57. However, due to the pointed end of the projections 57 and the acute angular disposition of the projections 57, the projections 57 engage and resist separation of the optical fibers 22 through the end 53 of the ferrule 45.

The formation of the connector end of the fabric 20 into a ferrule-like connector, without the use of a separate metal connector as in previous fiber optic light assemblies, enables the fabric cloth 20 to be cut with straight edges. This eliminates the need for extra lengths of fabric material to create the long fiber optic strands which have been joined in the prior art by means of a ferrule. The prior use of extra lengths of long strands of fiber optic material has made material handling awkward. The material also unravels from the cut ends thereby increasing waste and resulting in ruined products.

The fabric 20, with the bundled end connector 26 formed in a ferrule-like configuration described above, can be adhered by ultrasonic welding, spray glue adhesives, etc., to other backing fabrics for better handling, cutting and sealing. A big benefit using the present ferrule-like connector end 26 is that the connector end 26 can be easily formed with or without backing material included in the ferrule-like connector end 26.

A major benefit by the ferrule-like connector end 26 is that it minimizes stress points by distributing them within the bundled end 26. This increases the durability of the product, enables less labor-intensive work to form the ferrule, and allows non-factory usage and repairs without special crimping tools.

Referring now to FIGS. 7 and 8, there is depicted an alternate ferrule 300. The ferrule 300 is formed of a rigid material, such as a rigid plastic. The ferrule 300 is in the form of a one-piece body having a first end 302 which may have an outer diameter greater than the outer diameter of a body 304 of the ferrule 300. The body 304 includes at least two circumferentially spaced legs 306 and 308 which form a slot like aperture in the body 304 extending from an of the body 304 opposite from the first end 302.

Figure 32:
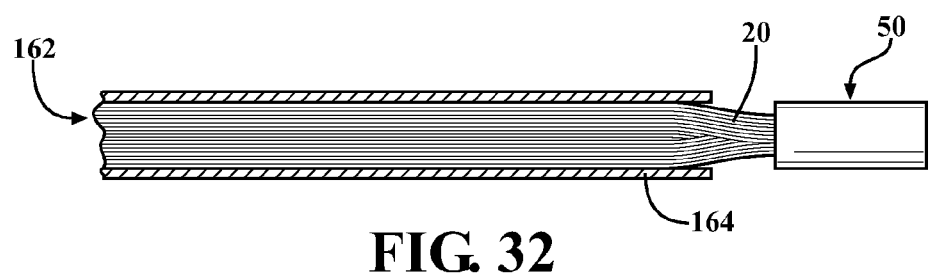
FIG. 32 is a side elevational, cross sectional view showing another aspect of an attachment member.

A pair of projections 310 and 312, each having an angled or smoothly curved end 314 and 316, respectively, are respectively formed at the ends of each leg 306 and 308. The surfaces 314 and 316 engage the end of the aglet 31 as the aglet 31 and the ferrule 300 are engaged and urged toward each other. Since the inner surfaces of the projections 310 and 312 are spaced closer together than the outer diameter of the end of the aglet 31, the end of the aglet 31 forces the legs 306 and 308 radially outward allowing insertion of the aglet 31 into the interior of the body 304. When the exposed ends of the fiber optic rods 22 engage the first end flange 302 of the ferrule 300, the opposite end 318 of the aglet 31 will slip behind the inner surfaces of the projections 310 and 312 allowing the legs 306 and 308 to snap back to there nominal position engaged with and tightly securing the aglet 31 within the interior of the ferrule 30 as shown in FIG. 32.

Any forces acting on the ferrule 300 or the fabric 20 in a direction intending to separate the ferrule 30 from the fabric 20 will be resisted of the engagement of the inner ends of the projections 310 and 312 with the end 318 of the aglet 31 thereby securely maintaining the ferrule 300 on the aglet 31.

A modification to the leg structure in the ferrule 300 is shown in the ferrule 330 depicted in FIG. 9. The ferrule 330 also has an enlarged diameter first end portion 332 and an adjacent body 334. The body 334 includes at least two circumferentially spaced legs 336 and 338 in which terminate end projections 340 and 342.

In this aspect, the legs 336 and 338 normally project at non-parallel angles with respect to each other and the first end 332 of the ferrule 330. This provides an enlarged opening between the ends of the projections 340 and 342 allowing easier insertion of the aglet 31 into the ferrule 330. The inner surfaces 344 and 346 of the projections 340 and 342, respectively, have inward angled surfaces which act to urge the legs 336 and 338 radially outward during engagement of the ferrule 330 with the aglet 31 until the aglet 31 has been inserted sufficiently within the interior of the ferrule 330 until the end 318 of the aglet 31 slips past the inner edge of the projections 340 and 342 allowing the inner edges of the projections 340 and 342 and the legs 336 and 338 to snap radially inward securely capturing the aglet 31 within the body 334 of the ferrule 330.

Yet another ferrule construction 360 is shown in FIGS. 10 and 11. The ferrule 330 also includes an enlarged diameter first end 362 and an adjacent body 364. An interior bore 366 extends through the body 364 from the first end 362 to an opposed second end 368. A hinged flap or door 370 is pivotally coupled to the second end 368 of the body 364 by a living hinge 372. An aperture 374 in the flap 370 is alignable with and has substantially the same diameter as the diameter of the bore 366 in the body 364.

Figure 34B:
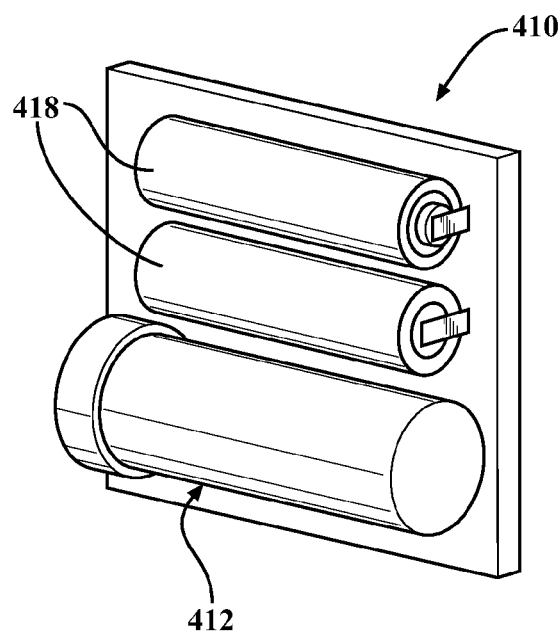
FIG. 34B is a perspective view of the light, control and power source portion of the apparatus shown in FIG. 34A.
Figure 34A:
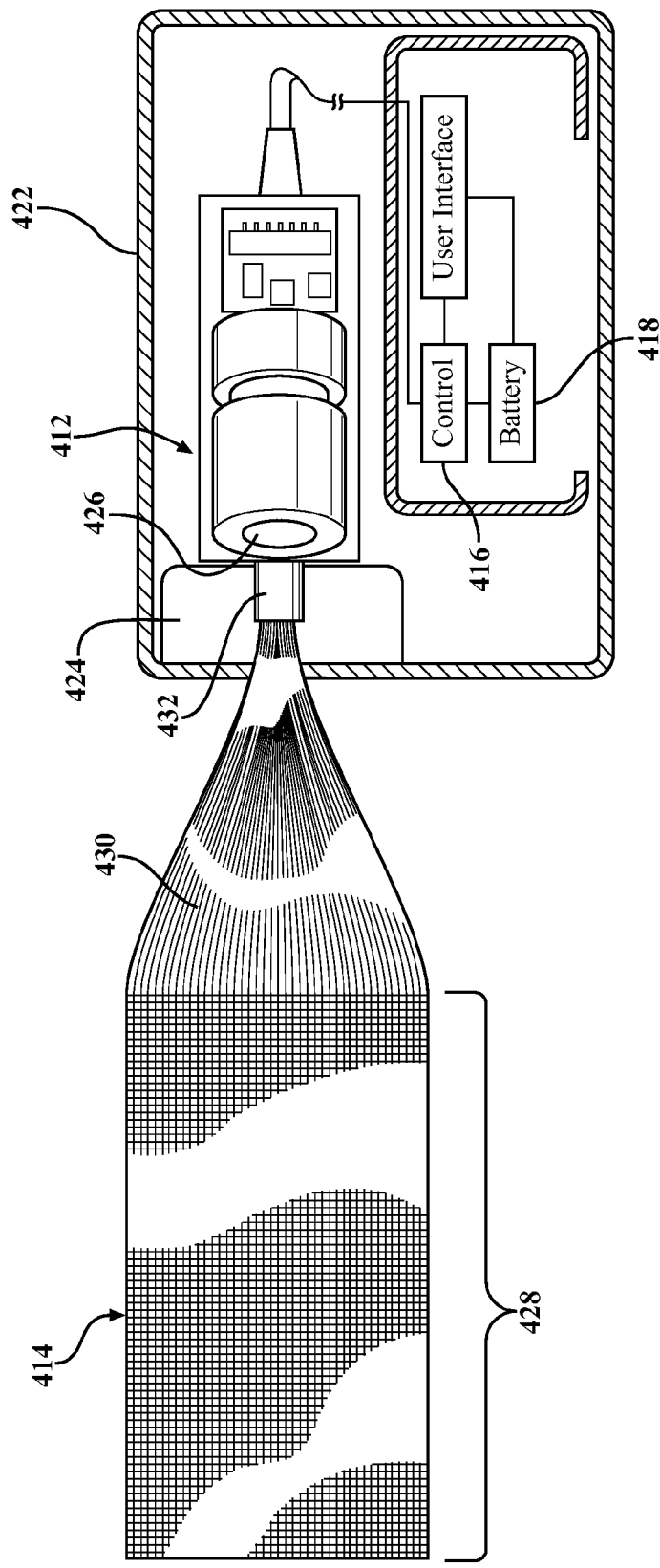
FIG. 34A is a block and pictorial representation of one aspect of a light therapy apparatus.
Figure 34C:
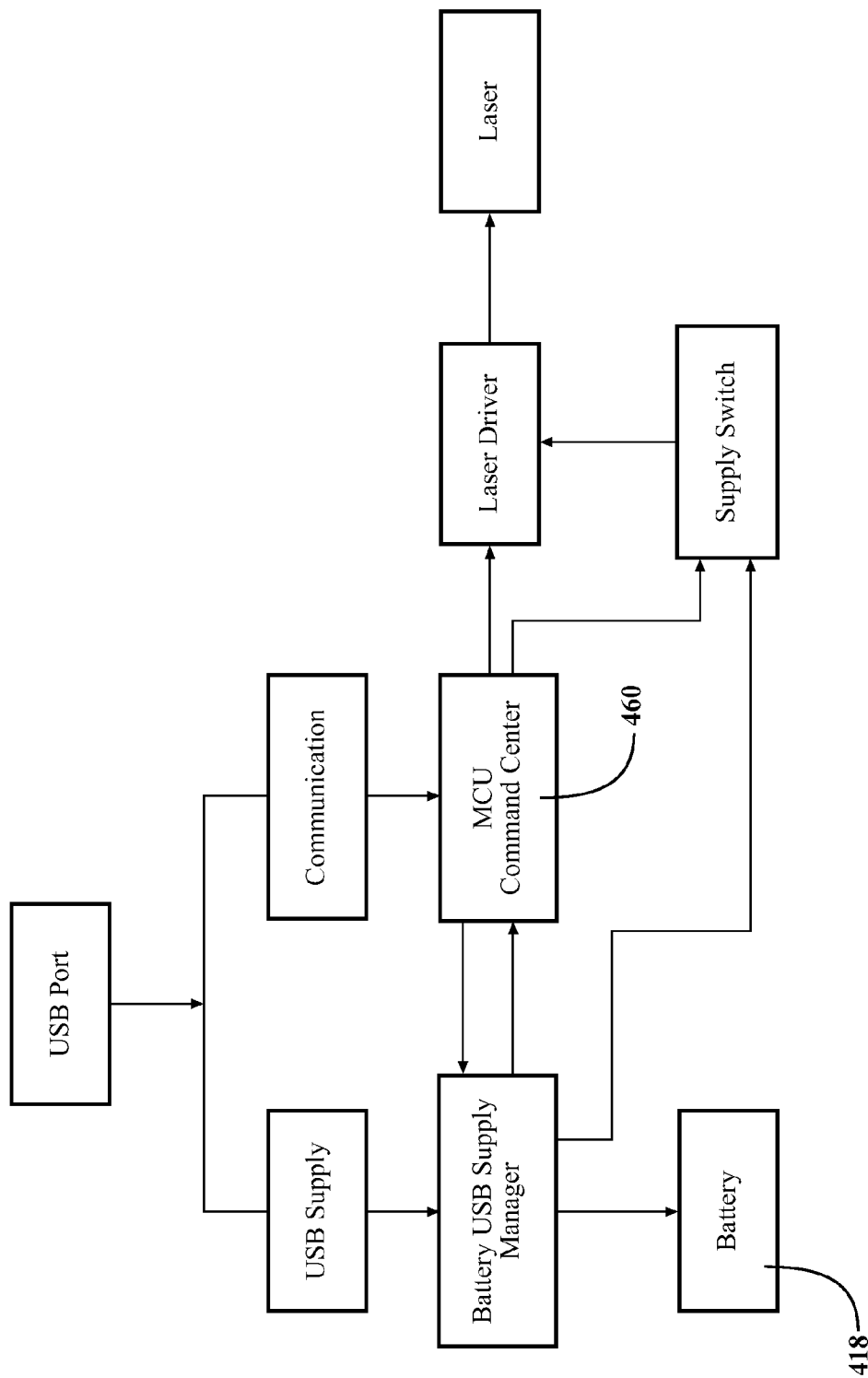
FIG. 34C is a blocked diagram of the controls carried in the light housing shown in FIG. 34B.

The living hinge 372 normally positions the flap 370 in an angularly spaced position from the second end 368 as shown in FIG. 34. When the ferrule 360 is to be mounted on the aglet 31, the flap 370 is pivoted about the hinge 372 into contact with the second end 368 of the body 364. This aligns the aperture 374 with the bore 366 allowing easy insertion of the aglet 31 into the bore 366. When the aglet 31 is fully inserted into the bore 366, the pressure on the free end of the flap 370 is released allowing the hinge 372 to pivot the flap 370 to a slightly angularly spaced position from the end 368 as shown in FIG. 11. In this position, the inner surfaces of the aperture 374 in the flap 370 engage the exterior of the optical fibers 22 and the fabric 20 thereby securely holding the ferrule 360 on the aglet 31. Any forces acting on the ferrule 360 or the fabric 20 tending to separate the ferrule 360 from the fabric 20 will cause the flap 370 to pivot further away from the second end 368 of the body 364 adding additional force to the engagement between the inner surface of the aperture 374 in the flap 370 and the fabric 20 to resist any separation of the ferrule 360 from the fabric 20.

Figure 12:
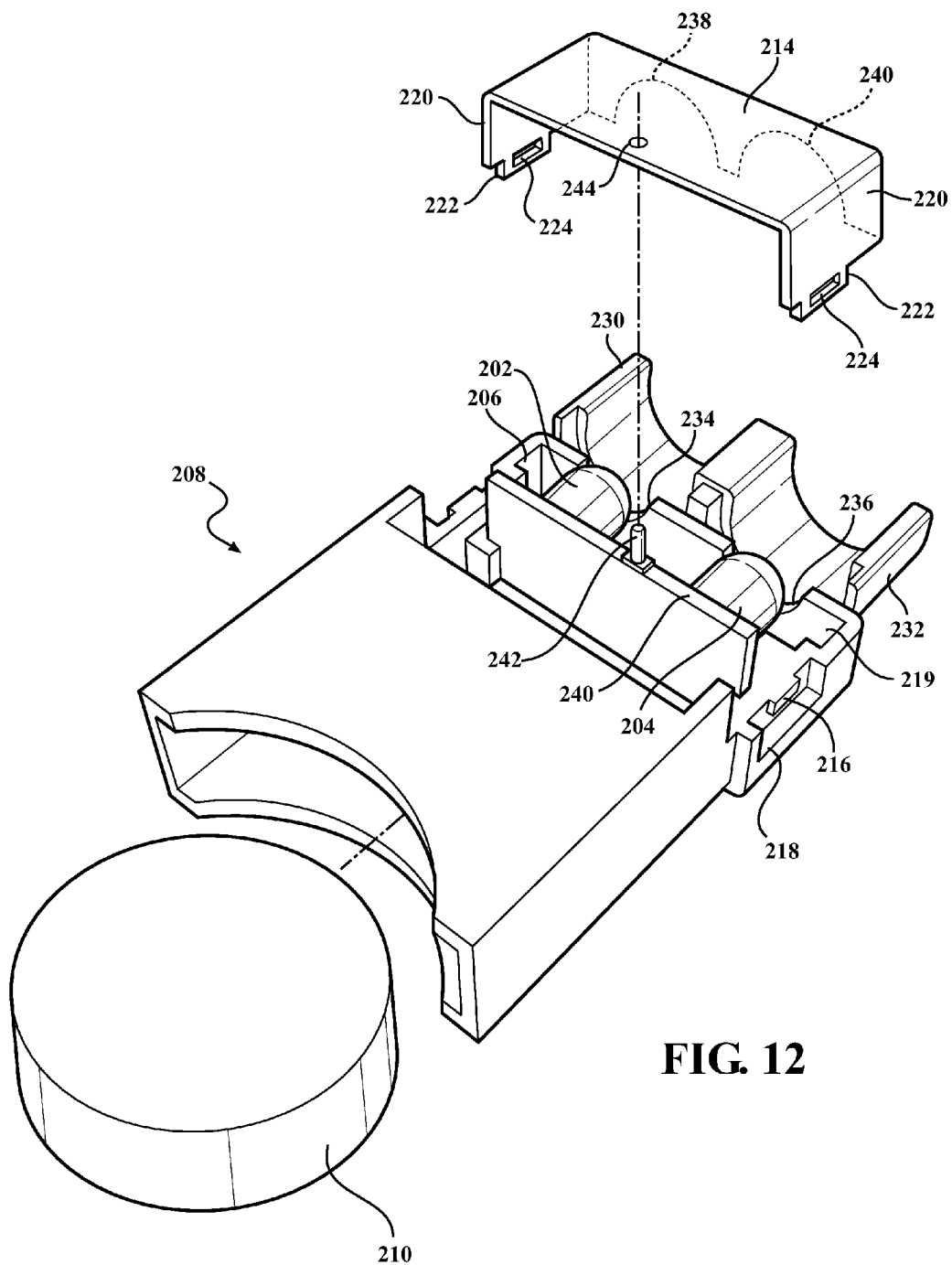
FIG. 12 is an exploded perspective view of one aspect of a light source and power supply holder.
Figure 13:
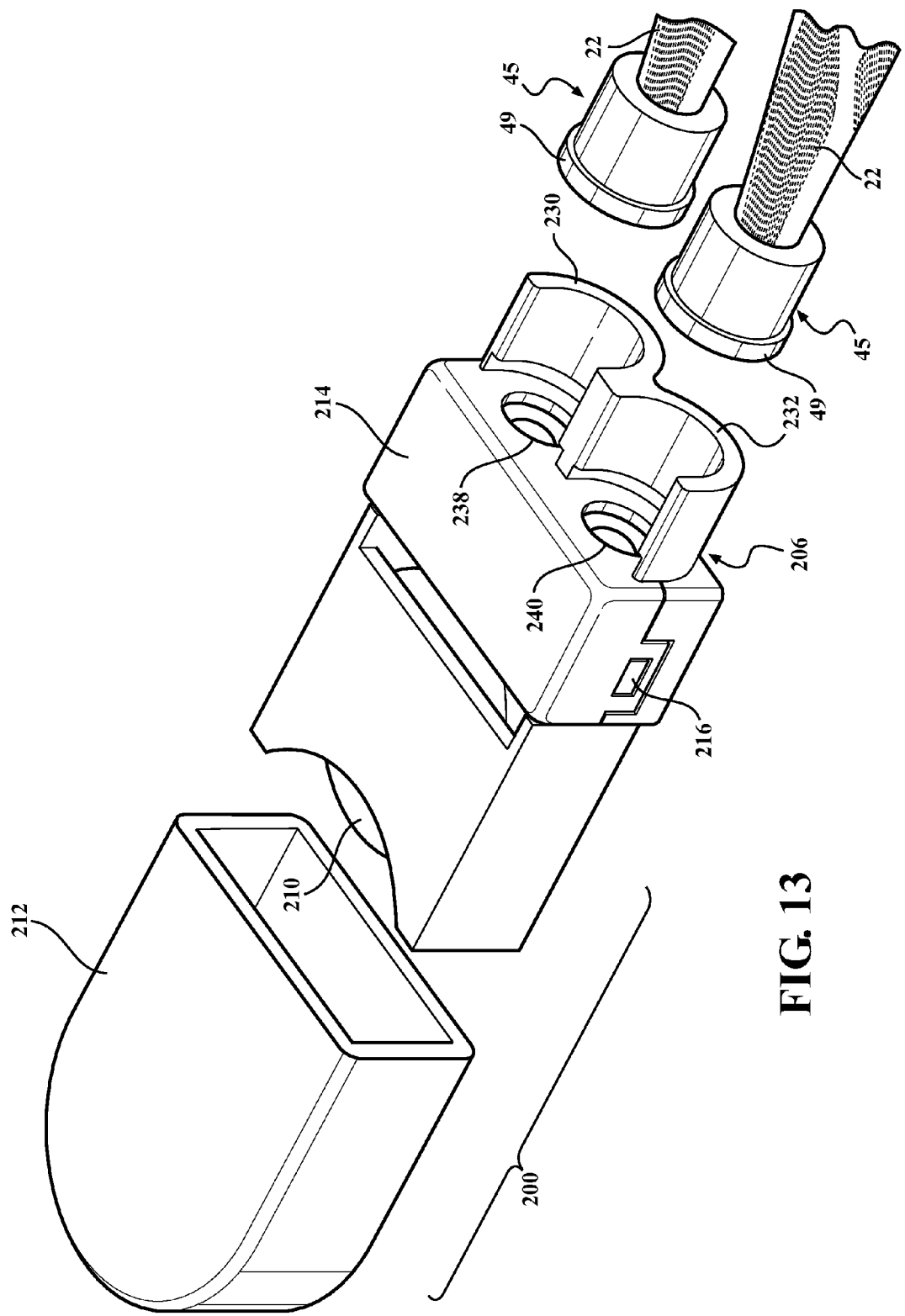
FIG. 13 is an exploded perspective view showing the attachment of ferrules on a bundled end of an optical fabric to the holder shown in FIG. 12.

A holder 200 is depicted FIGS. 12 and 13. The holder 200 is adapted for receiving at least one or two light sources 202 and 204, such as LED's or lasers, within one section 206 of the holder 200. The one section is also configured for removably receiving at least one or two ferrules 45 each mounted on the bundled end 26 of optical fibers 22 as described above. The first section 206 of the holder 200, places the ends of the optical fibers 22 in an optimum spacing with the light sources 202, 204 in the one section 206 of the holder 200 for optimum light transmission.

A second section 208 of the holder 200 acts as a receptacle for an electrical power source, such as one or more batteries 210.

A cover 212 shaped complimentary to the second section 208 is slidable mountable over the exterior of the second section 208 to cover the battery 210. The cover 212 is frictionally held on the second section 208 in a tight interference fit.

Similarly, as shown in FIG. 13, a cover 214 is mountable over the portion of the first section 206. Latch projections 216, only one of which is shown in FIG. 13, are formed on opposite sidewalls of the first section 206. The projections 216 are disposed within notches 218 formed in the sidewalls of the first section 206.

The cover has an inverted U-shape formed with a pair spaced sidewalls 220 from which depend a pair of flanges 222, each containing an aperture 224 complimentary shaped to the shape of the projections 216. The cover 214 can be forcibly urged into engagement with the first section 216 by inserting the flanges 222 on the cover 214 into the recesses 218 in the sidewalls of the first section 206. The downward force urges the flanges 222 outward a slight amount to enable the flanges 222 to slide over the projections 216 until the projections 216 engage and seat within the apertures 224 in the flanges 222 to removably attach the cover 214 to a first section 216.

As shown in FIGS. 12 and 13, a pair of semi circular shaped receivers 230 and 232 project from one end of the first section 206 and the interior bores in the sleeves 230 and 232 are sized to removably receive the tubular sections of the ferrules 45. U-shaped apertures 234 and 236 are formed in an end wall of the first section 206 and form a generally circular opening with a pair of inverted U-shaped apertures 238 and 240 formed in an endwall of the cover 214. The apertures formed by the mating apertures 234 and 238, and 236 and 240 engage the tubular section of one ferrule 45 capturing the enlarged diameter flanged 49 within the interior cavity of the first section 206.

In use, the cover 214 is removed from the first section 206. One or more ferrules 45 are inserted into the receivers 230 or 232 with the enlarged diameter flange 49 seated up against the endwall 219 of the first section 206 of the holder 200. The cover 214 is then latched to first section 206 to capture the ferrules 45 within the receivers 230 and 232.

A circuit board 240 is mounted within U-shaped projections in the first section 206 of the holder 200. The circuit board 240 carries connections to the battery 210 as well as serving as a mount for the light sources, such as the LED's 202 and 204. An on/off or push button switch 242 is carried along one edge of the circuit board 240. The push button 242 projects through an aperture 244 formed in a top wall of the cover 214 to provide on/off operation of the light sources 202 and 204.

In the aspect of the holder 200 shown in FIG. 13, the one or two light sources 202, 204 and the receivers 230 and 232 for receiving the ferrules 45 at one bundled end of optical fibers 22 are arranged in parallel with each other and to the longitudinal axis of the holder 200.

Figure 14:
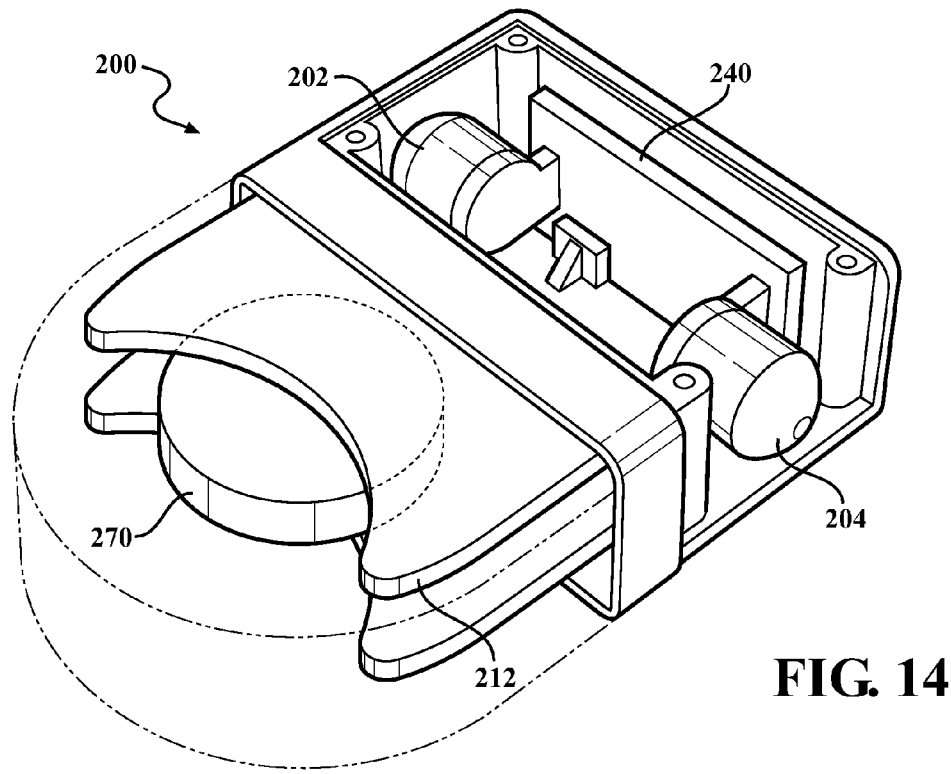
FIG. 14 is a perspective view of another aspect of a light source and power supply holder.
Figure 15:
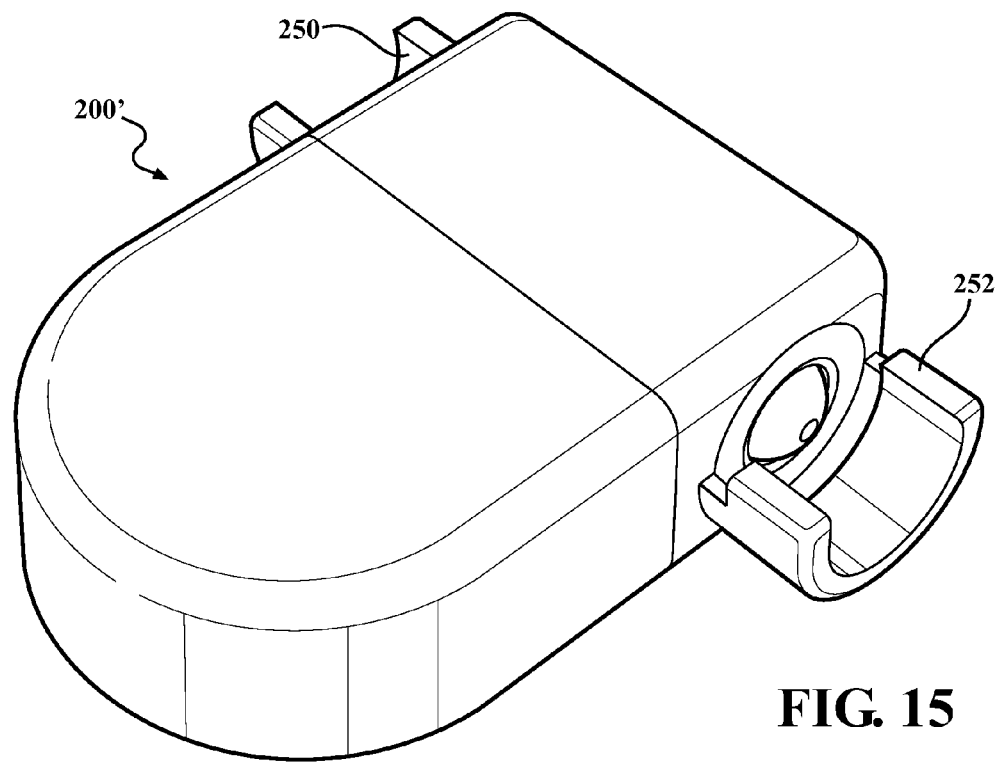
FIG. 15 is an exploded view of the holder shown in FIG. 14.

As shown in FIGS. 14 and 15, the first section of a holder 200' can be modified so that the receptacles 250 and 252 which receive the ferrules 45 on one bundled end of a plurality of optical fibers 22 are arranged in a different angular orientation, such as perpendicular to a longitudinal axis through the holder 200'. It will be understood that the receptacles 250 and 252 may also be disposed at any other acute or obtuse angle with respect to the longitudinal axis of the holder 200' for transmitting light in a desired direction along the optical fibers mounted in the receptacles.

Figure 16:
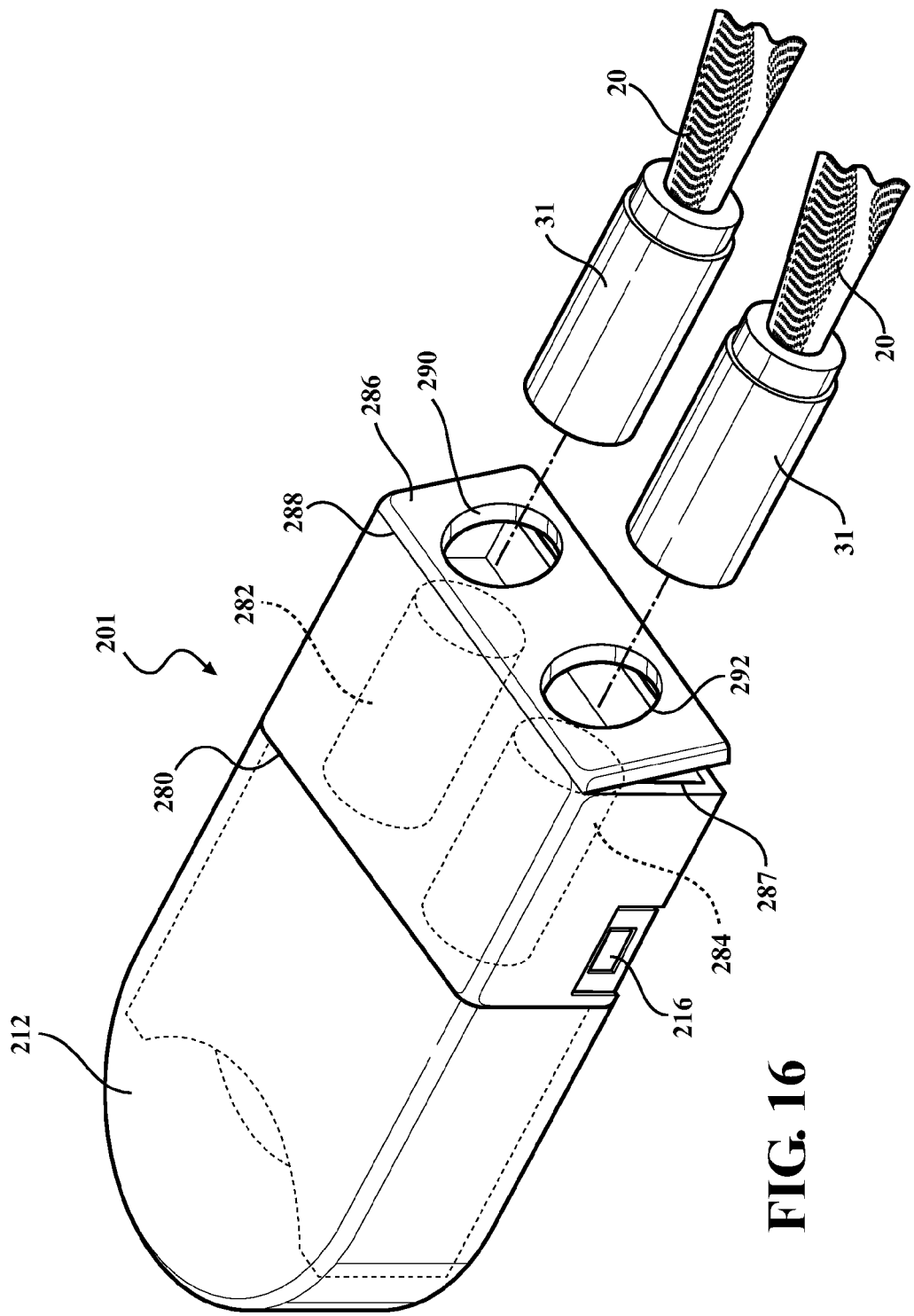
FIG. 16 is an exploded perspective view of another aspect of a holder.

A modified holder 201 is shown in FIG. 16. The holder 201 is substantially similar to the holder 200 in that it includes a cover 214 removably mountable over the second section 208 containing the power source or batteries 210 and a cover 280 mountable over a first section of the holder 201.

In the holder 201 shown in FIG. 16, the receptacles 230 and 232 are formed wholly within the first section 206 in the form of completely enclosed bores 282 and 284. A pivotal door 286 is coupled to one end of the cover 280 by a hinge, such as an integral living hinge 288. The cover 286 includes a pair of apertures 290 and 294 which align with the bores 282 and 284, respectively, within the first section of the holder 201. It is a natural tendency of the living hinge 288 to normally position the cover 286 in the spaced apart, angular position relative to the end 287 of the first section of the holder 201. In this position, the edges surrounding the apertures 290 and 292 in the cover 286 engage the fabric 20 adjacent an end of the ferrules 31 to forcibly retain the ferrule 231 in position within the bores 282 and 284 in the first section of the holder 201 in optimum light transmission position relative to the light sources within the first section of the holder 201.

To insert or remove the ferrules 31 from the holder 201, the door 286 is urged into engagement with the end 287 of the first section of the cover 280. This aligns the apertures 290 and 292 in the door 286 with the respective bores 282 and 284 in the holder 201 to enable the ferrules 31 to be easily inserted through the apertures 290 and 292 into the bores 282 or 284 or pulled therefrom.

When the ferrules 31 are in a fully inserted position within the bores 282 and 284 in the holder 201, the pressure on the door 286 is released allowing the door 286 to pivot about the living hinge 288 to its nominal position in which the inner edges of the door 286 surrounding the apertures 290 and 292 frictionally engage the fabric 20 to retain the ferrules 31 in a fixed position in the holder 201.

Figure 17:
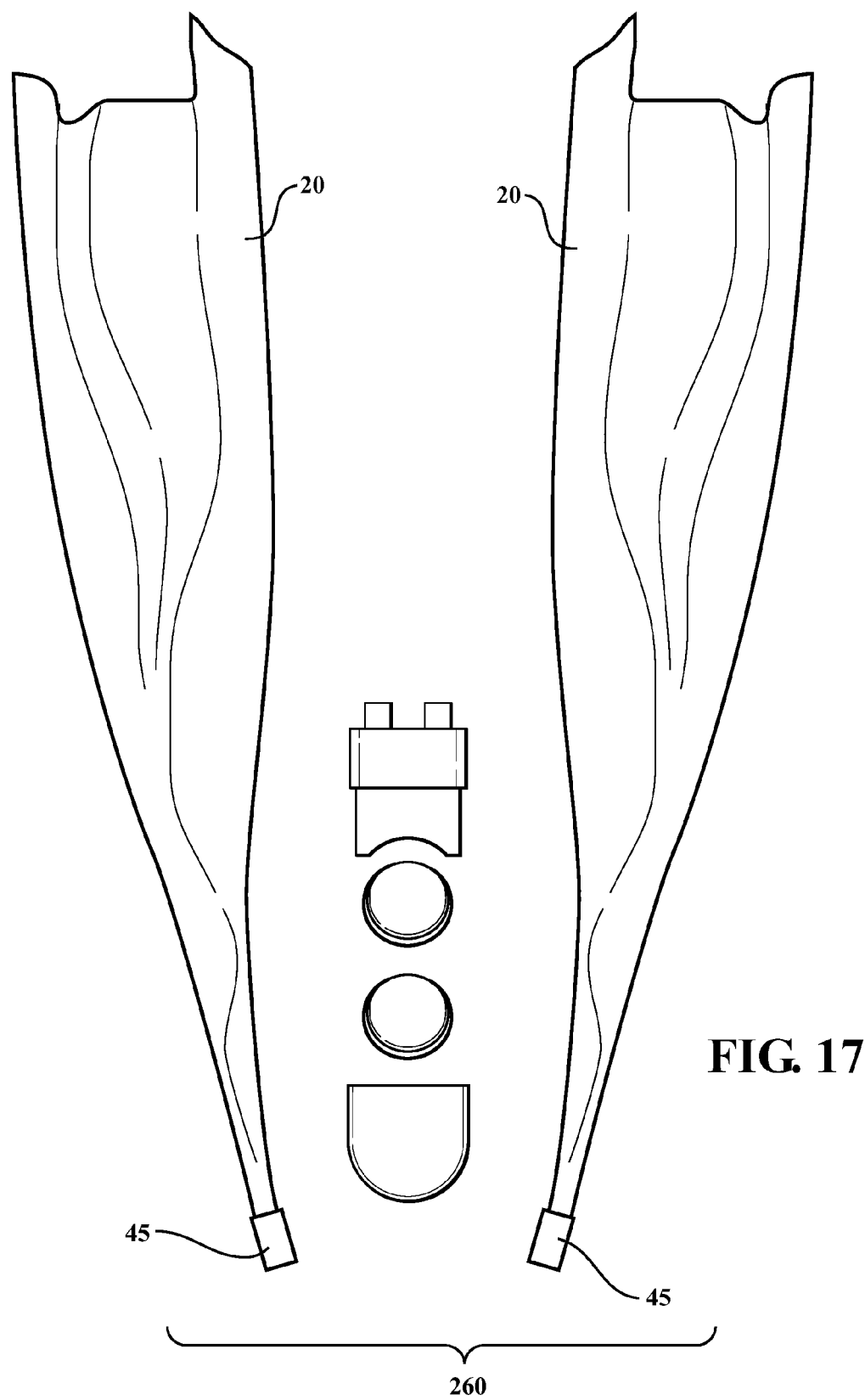
FIG. 17 is a pictorial representation of a kit of components for forming an illuminatable article.

As shown in FIG. 17, a kit 269 is formed of the various components for use as a single product. The kit 260 can include the holder 200 or 200' with the required number of batteries. The kit 260 would also include one or more predetermined lengths of optical fiber textile product 20, such as two products 20 for example, each being any length, such as 8 inches, 12 inches long, etc. being provided. One end of the optical fibers 22 in the fabric 20 is tightly bound in a ferrule 45, 302, 330, 360, etc. Since the illustrated example of the holder 200 includes two receptacles for receiving two optical fiber bundles, two lengths of optical fabric 20 can be provided in the kit, it will be understood that different numbers of holders as well as a corresponding number of optical fabric strips of any length may also be provided in the kit 260.

Figure 18:
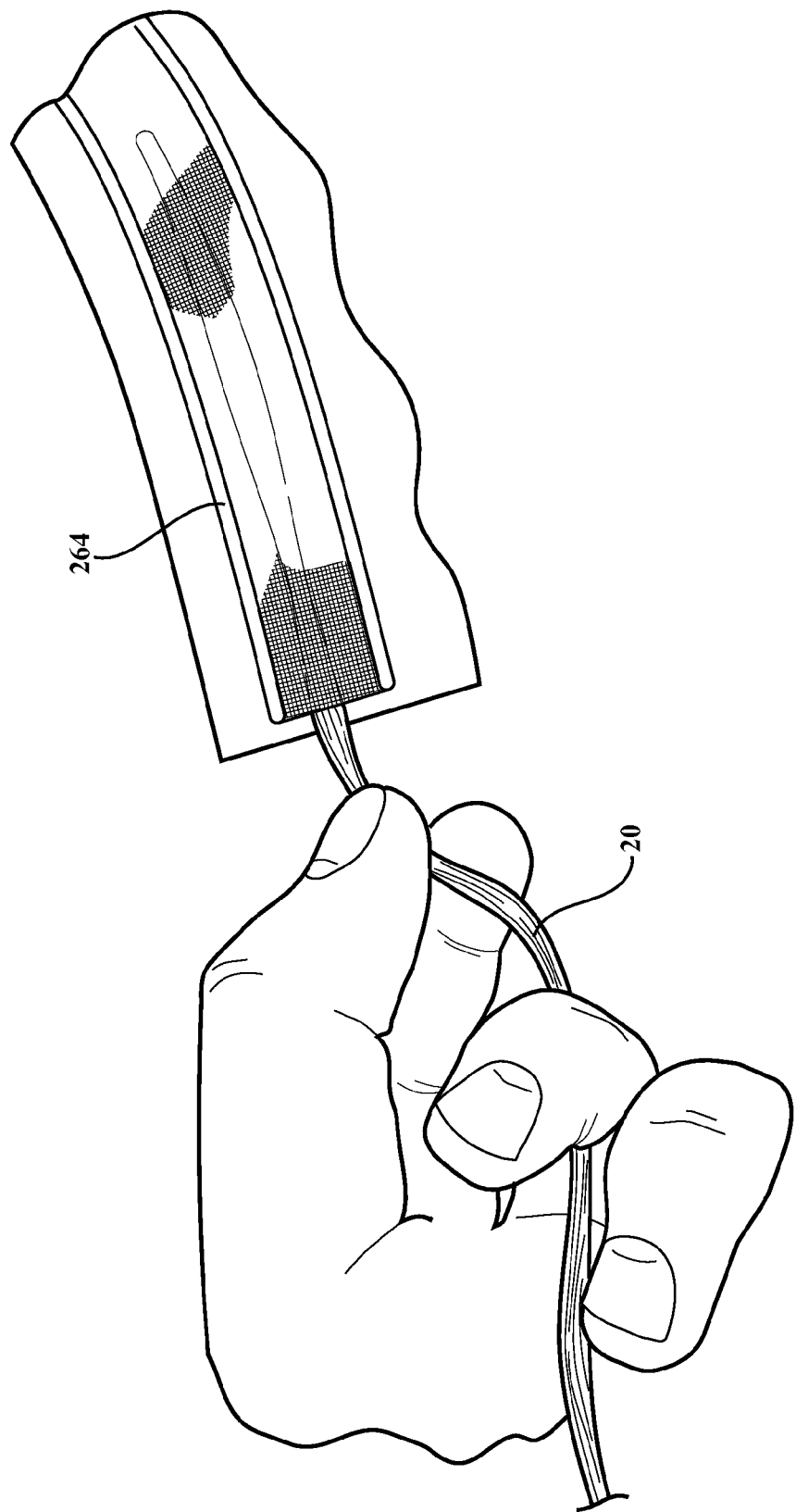
FIG. 18 is a pictorial representation of another aspect of an illuminated article.

The kit 260 enables a user to mount the optical fabric product(s) 20 on any garment or article the user desires. For example, as shown in FIG. 18, the optical fabric 20 may be tightly overlaid or wound into having a generally circular cross section which is then inserted into an opaque, semi-transparent or transparent hollow rib 264 as shown in FIG. 18. The rib 264 is similar to the welt strip found on fabric furniture and clothes. Threads, glue, etc., attach the ribbing 244 to an exterior or interior surface of an article of clothing, such as the jacket, for example. One or more ribs 264, each with a separate wound optical fabric 20, therein, may be disposed in close proximity along a portion of the garment to provide illumination when the user is wearing the garment. This is particularly useful when the garment is an article of clothing worn by a runner, cyclist, construction worker, emergency worker, etc.

The kit 260 can also be formed of one or more fabric products 20 of any length. A shrink tube may be included in the kit 260 along with a tube or container of adhesive such as cyanoacrylate adhesive. This enables a user to cut the fabric 20 to a desired length, and fix the tube over the bundled end of the fabric to form a ferrule and then apply the end product and holder to any article chosen by the user.

Figure 21:
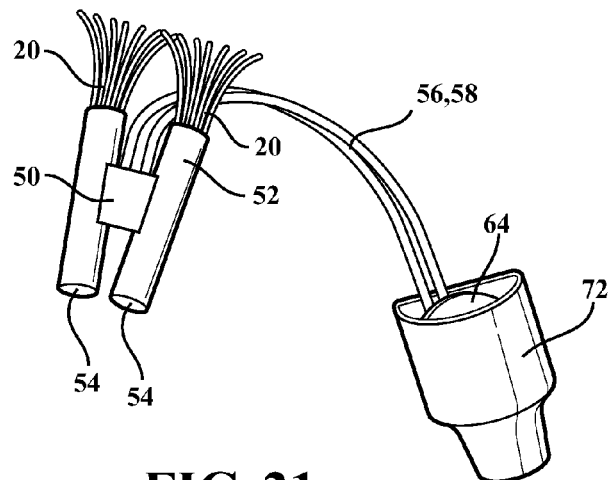
FIG. 21 is a pictorial representation of another aspect of an illuminated article.

Referring now to FIG. 21, the sleeve or aglet 32 or simply the exposed adhesively joined ends 46 of the optical fibers 22 in the bundled end 26 can be inserted into a holder assembly 50. One holder assembly 50 is provided for each bundle 46 of optical fibers 22. Two holders 50 are shown in FIG. 21 for use with two separate fiber optic bundles 26 formed into the connector 46 from two different fabric articles 20.

The holders 50 comprise a generally cylindrical tube having opposed open ends and internal through bore. The holder may be formed of a thin rigid plastic, for example.

The bore extending from one end 52 of each holder 50 may have a tapered cross section extending, for example, from a 6 mm inner diameter at the end 52 to a 5 mm diameter internally within the bore of the holder 50.

An individual light source 54 is fixably inserted into the opposite end of the holder 50 to be disposed in a specific dimensional relationship with the ends 38 of the optical fibers 22 in the fabric 20 mounted in the same holder 50. The light source 54 can be any suitable light source, such as the LED shown in FIG. 22. LED's 54 having any suitable wavelength and therefore any visible colors can be employed.

Figure 22:
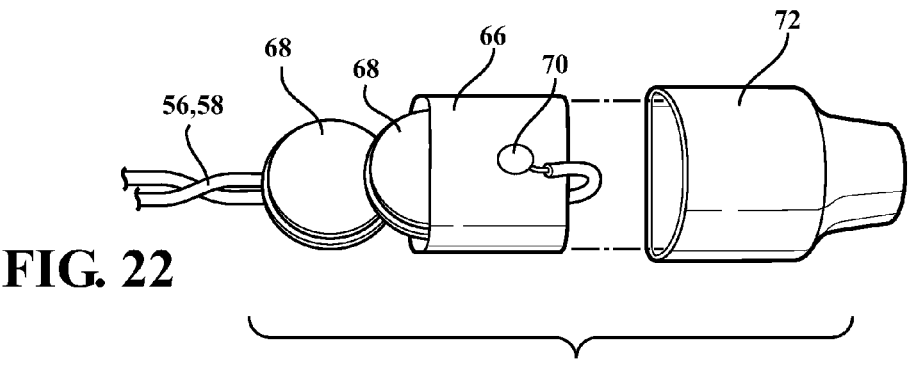
FIG. 22 is an exploded perspective view of the power supply portion of the illuminated article depicted in FIG. 21.

Electrical power is supplied to the light sources 54 through a pair of electrical conductors 56 and 58 extending to connections mounted at one end of the holders 50 or to terminals mounted on a circuit board or a fixed plate joined to the plurality of holders 50 shown in FIG. 22.

The opposite ends of the conductors 56 and 58 are connected to a battery assembly 64 as shown in FIGS. 21 and 22. The battery assembly 64 includes a case 66 which removably receives one or more battery cells 68, with two battery cells 68 shown by way of example only in FIG. 23. Electrical connections 70 are formed in the case 66 and receive the ends of the conductors 56 and 58. The case 66 and the batteries 68 are mounted in a protective cover 72.

Figure 23:
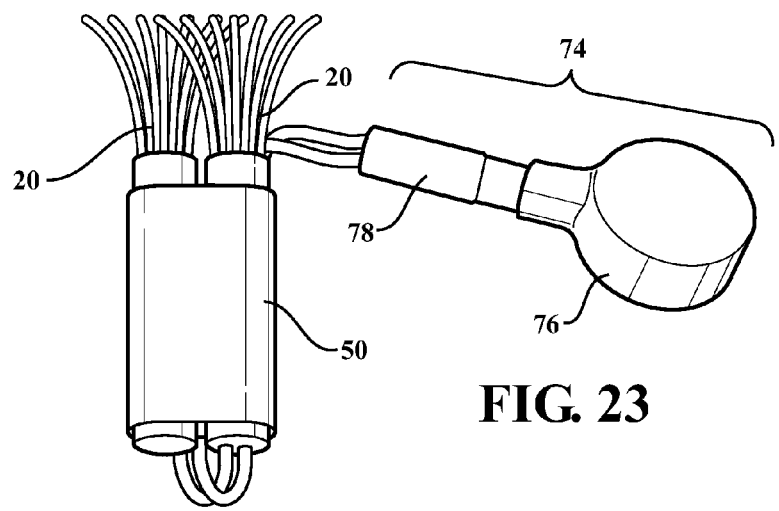
FIG. 23 depicts an alternate power supply assembly for the holder shown in FIG. 21.

FIG. 23 depicts an alternate battery assembly 74. In the battery assembly 74, one or more battery cells, not shown, are removably mounted in a case 76 which has an openable portion allowing access to a battery receiving cavity within the interior of the holder 76. Electrical connections from the battery case 76 extend through a sleeve or ferrule 78 to the light source holders 50.

Figure 24:
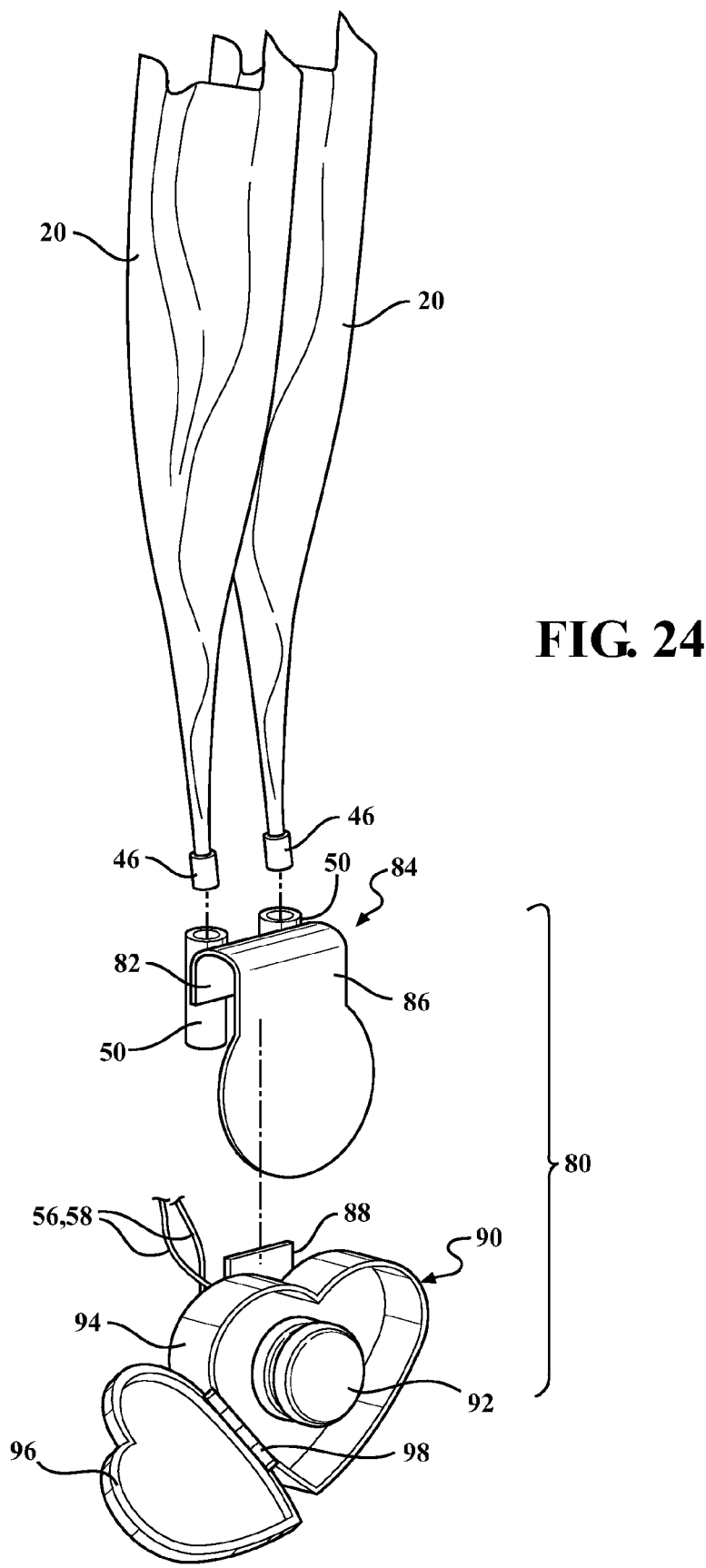
FIG. 24 is an exploded perspective view of another aspect illuminated article.

Referring now to FIG. 24, there is depicted another apparatus 80 for coupling light from a light source to the bundled ends 46 of the optical fibers 22 in a fabric sheet 20.

One holder 50 is provided for each bundled end 46 of the optical fibers 22. The holders 50 are joined to one end portion 82 of an attachment member or clip 84. The attachment member 84 has a generally inverted U-shape.

The opposite end 86 of the attachment member 84 is fixedly, removably, or pivotally attached to a flange or portion 88 of a decorative member 90 which serves as a battery compartment for one or more battery cells 92.

The decorative article 90 is shown by way of example only as having a heart shape. Any other decorative shape for a pendant, necklace, etc., may be formed to use the decorative article 90.

The decorative article 90 may be formed with pivotal halves or portions 94 and 96 which are connected together by a hinge 98. Alternately, the decorative member 90 may be a single piece member with an opening along one edge allowing removable insertion of the battery cells 90 into the interior of the decorative article 90 as well as providing suitable access to the battery cells 92 for removal from the decorative article 90.

Internal battery contacts, not shown in FIG. 24, are fixed within the interior of the decorative article 90 and are electrically connected to the conductors 56 which extend to the light source holders 50.

The arrangement 80 shown in FIG. 24 enables connection of the bundled end 46 of the illuminated fabric 20 to the light sources in the holders 50; while enabling easy removal of the fabric 20 from the holders 50 to allow cleaning of the fabric 20 or the article in which fabric 20 is disposed without damaging the LED's or batteries.

FIG. 25-28 depicts alternate mounting configurations of the holders 50 and a battery assembly, such as battery assembly 64 shown in FIG. 21.

Figure 25:
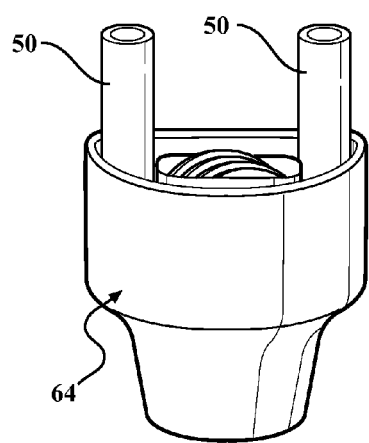
FIG. 25 is another aspect of an alternate holder and power supply assembly.

In FIG. 25, the holders 50 extend substantially in parallel from one end of the battery compartment 64. When this configuration is employed with the attachment member 84 shown in FIG. 5, the holders 50 will typically be disposed in a vertical orientation on the user.

Figure 26:
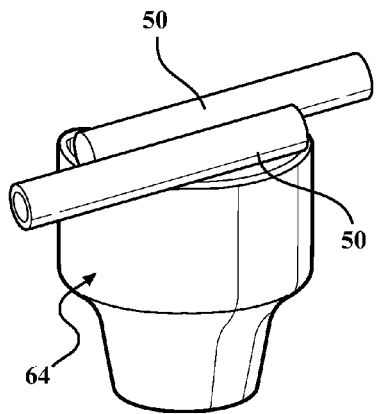
FIG. 26 is a perspective view of another aspect of a holder.

FIG. 26 depicts what is termed a "horizontal" orientation of the holders 50. In this configuration, the optical fiber receiving ends of each holder 50 are disposed in opposite facing directions on the battery compartment 64.

Figure 27:
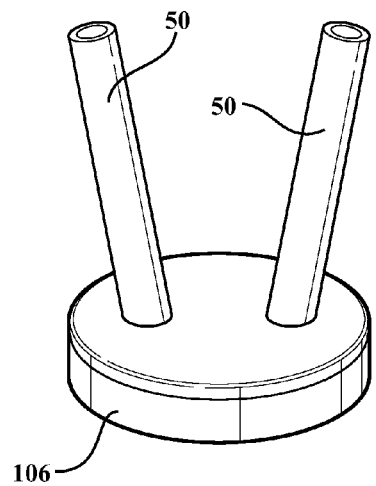
FIG. 27 is a perspective view of yet another aspect of the holder.

In FIG. 27, the holders 50 are disposed at an outward diverging, non-parallel angle from an attachment end to a circular battery compartment 106.

Figure 28:
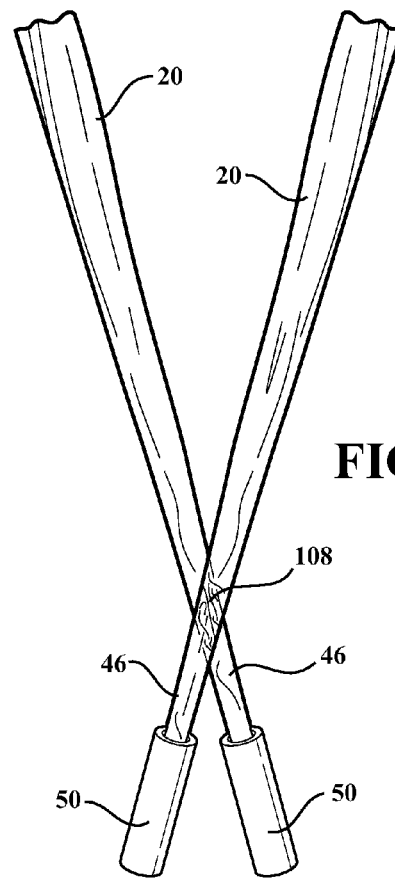
FIG. 28 is a perspective view of yet another aspect of the holder.

In FIG. 28, the pair of holders 50 are disposed in a fixed angular arrangement on a suitable support or battery compartment, not shown, such that the bundled ends 46 and the optical fibers in the fabrics 20 overlay each other in a crisscross configuration to form a highly illuminated hot spot 108 which will have greater light intensity output than the light being emitted from the remainder of the optical fibers 22 in each fabric 20.

Figure 29:
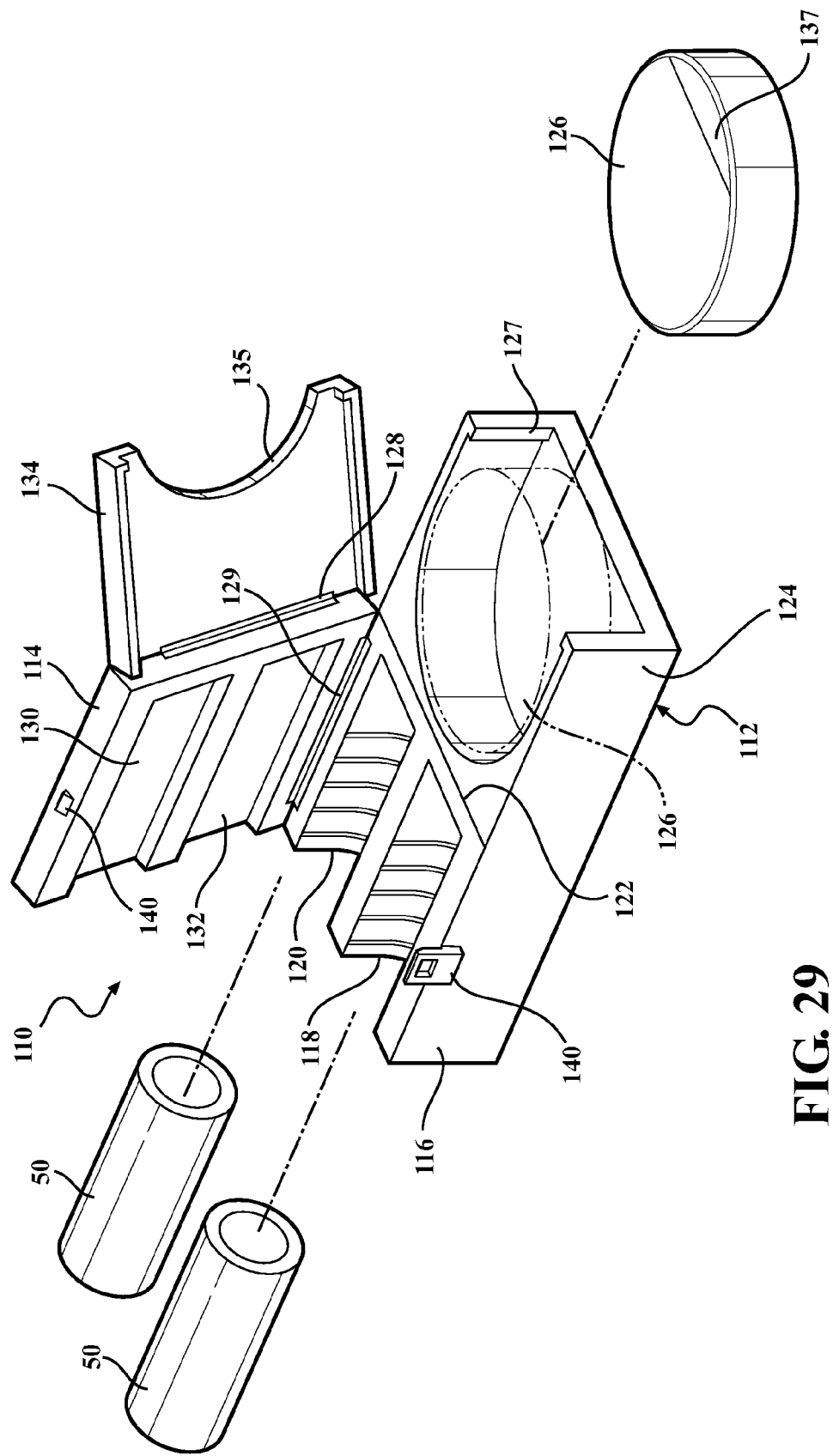
FIG. 29 is an exploded perspective view of yet another aspect of a holder.

Another aspect of a light source and optical bundle receptacle 110 is shown in FIG. 29. In this aspect, the receptacle 110 provides the dual functions of removably receiving the one or more separate holders 50 and the batteries 126. The receptacle 110 has two removably connected housing portions 112 and 114.

The first housing portion 112 is in the form of a generally planer member having a first end 116 with receptacles 118 and 120, each sized to removably receive a holder 50. A divider wall 122 separates the first end 116 of the housing portion 112 from a second end 124 which serves as compartment for receiving one or more battery cells 126. Electrical wires, not shown, or a circuit board, also not shown, may be disposed within the first housing portion 112 for supplying electric power from the battery cells 126 to the light sources mounted in the holders 50.

The first housing portion 112 is movably coupled to the second housing portion 114 by a hinge 128 which may be a living hinge integrally formed between the first and second housing portions 112 and 114.

The interior of the second housing portion 114 is generally a mirror image of the first housing portion 112 in that the second housing portion 114 includes a pair of cavities 130 and 132 in one end 129 sized to removably receive one or more holders 50. The second end 134 of the second housing portion 114 is pivotally connected by a hinge 136, such as a living hinge, to the first end 129. The second end 134 also serves as a cover for the battery compartment in the first housing portion 112.

In use, the holder 110 will initially be in the orientation shown in FIG. 29, with the second housing 114 is pivoted away from the first housing portion 112. This allows insertion or removal of the holders 50 as well as insertion or removal of the battery cells 126. After the holders 50 and battery cells 126 have been inserted into the first housing portion 112, the second housing 114 is pivoted about the hinge 128 over and latched to the first housing portion by means of a suitable latch clip 140 carried on one or both of the first and second housing portions 112 and 114 which engages a lip on the opposed housing portion 112 or 114.

A similar latch clip and lip is provided on the second end 134 of the second housing portion 114 to enable the second end 134 to be pivoted about the hinge 136 to an open position allowing access to the battery cells 126 for removal or insertion without disturbing the fixed placement of the holders 50 in the opposite ends of the holder 110.

As also shown in FIG. 29, a slot 127 may be formed in the endwall of one or both of the housing portions 126 and 134, which cooperate to form the battery compartment in the holder 110. The width of the slot 127 may be slightly smaller than the diameter of the battery 126 so as to require a slight amount of force to insert the battery 126 into the holder 110; while preventing inadvertent slippage of the battery 126 from the holder 110 during use of the holder 110. Optionally, the entire holder 110 may be formed of a material which has a slight amount of exterior friction or stickiness to securely retain the battery 126 in the holder 110 after the battery 126 has been inserted into the slot 127.

A small generally U-shape notch 135 can optionally formed in the endwall of the second housing portion 134. The notch 135 allows an edge portion 137 of the battery 126 to be exposed and easily grasped by a user to facilitate removal of the battery 126 from the holder 110. This arrangement also enables the battery 126 to act as an on/off switch for the holder 110 through selective insertion and removal of the battery 126 from the holder 110. Further, the slot 127 may also be formed with a U-shape to enable two fingered grasping of the battery 126.

It should be noted in FIG. 29 that the outer ends of the cavities 118, 120, 130 and 132 can be formed with a plurality of retention fingers or barbs 140. The barbs 140 engage the ends of the holders 50 to forcibly retain the holders 50 within the housing 110.

At the same time, the barbs 140 can be formed so as to have their inner ends disposed at an inward extending angle from the endwall of the housing portions 118 and 129. This inward extending angle applies tension to the holders 50 to securely retain the holders 50 within the receptacles 118, 120, 130 and 132, when the holder 110 is in an open position as shown in FIG. 29.

In addition, the inward extending angle of the ends of the barbs 140 allows for easy insertion of the ferrule-like connector 26 through the opening formed between the inner ends of the barbs 140 and into the holder 50 mounted in the mating pairs of receptacles 118, 120, 130, and 132 and the holder 110. The inward tapered bore in the holder 50, as described above, in conjunction with the inward angles of the barbs 140 securely engage the connector end 26 of the fabric 20 to retain the connector 26 securely within the holder 50 in the holder 100 and prevent disengagement of the connector end 26 from the holder 50 and 110 during use.

Figure 30:
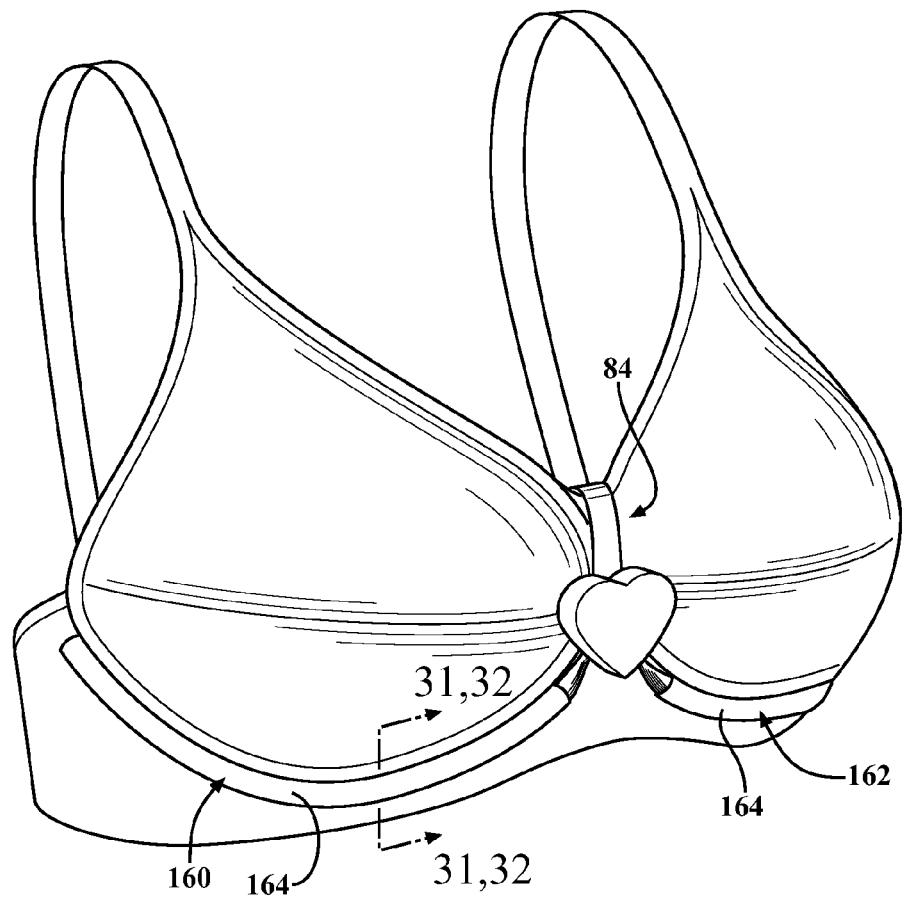
FIG. 30 is a perspective view of another aspect of illuminatable article.
Figure 31:
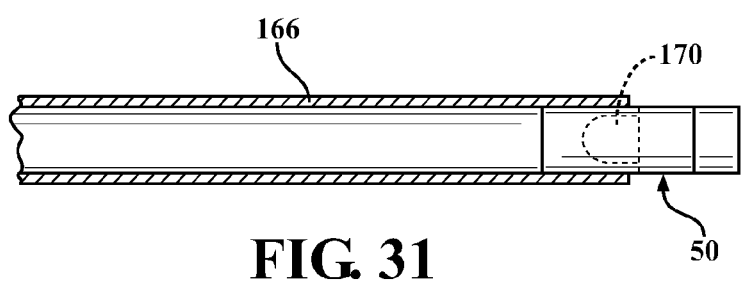
FIG. 31 is a side cross sectional view showing an attachment member mounted on the illuminatable article of FIG. 30.

Referring now to FIGS. 30-32, there is depicted exemplary uses of the light apparatus described above in various aspects on an article of clothing. The use of the light apparatus on a bra will be understood to be by example only as the light apparatus employing one or more optical fabric bundles may be employed on other articles such as different articles of clothing, hats, jackets, shoes etc.

As shown in FIG. 31, pairs 160 and 162 of fiber optic fabrics 20 are fixedly mounted along a lower edge of each bra cup. The fabric 20 is cut to the desired size and the edges heat sealed, such as by ultrasonic cutting. The fabric 20 forming each bundle 160 and 162 is folded back and forth on itself in one or more layers as shown in FIG. 3. The folds extend transverse to the longitudinal axis of the optical fibers 22 in each fabric bundle 160 and 162. The bound ends 46, as shown in FIG. 1G, of each fabric bundle 160 and 162 are mounted in the holders 50 of an attachment member, such as the attachment member 84 shown in FIGS. 24 and 30. The attachment member or clip 84 is removably mounted over the center portion of the bra as shown in FIG. 30.

As shown in FIG. 3, the illuminated fabric 20 is folded one or more times over itself along the longitudinal axis to the optical fibers 20. The folded over fabric 20 is mounted in a hollow plastic tube 164 which is preformed in shape or is bendable into the desired underwire shape shown in FIG. 32.

Alternately, as shown in FIG. 31, a light source 170, such as an LED, in a holder 50, for example, is fixedly attached to an open end of a hollow tube 166 which is preformed or can be shaped into the desired underwire shape shown in FIG. 32.

Figure 33:
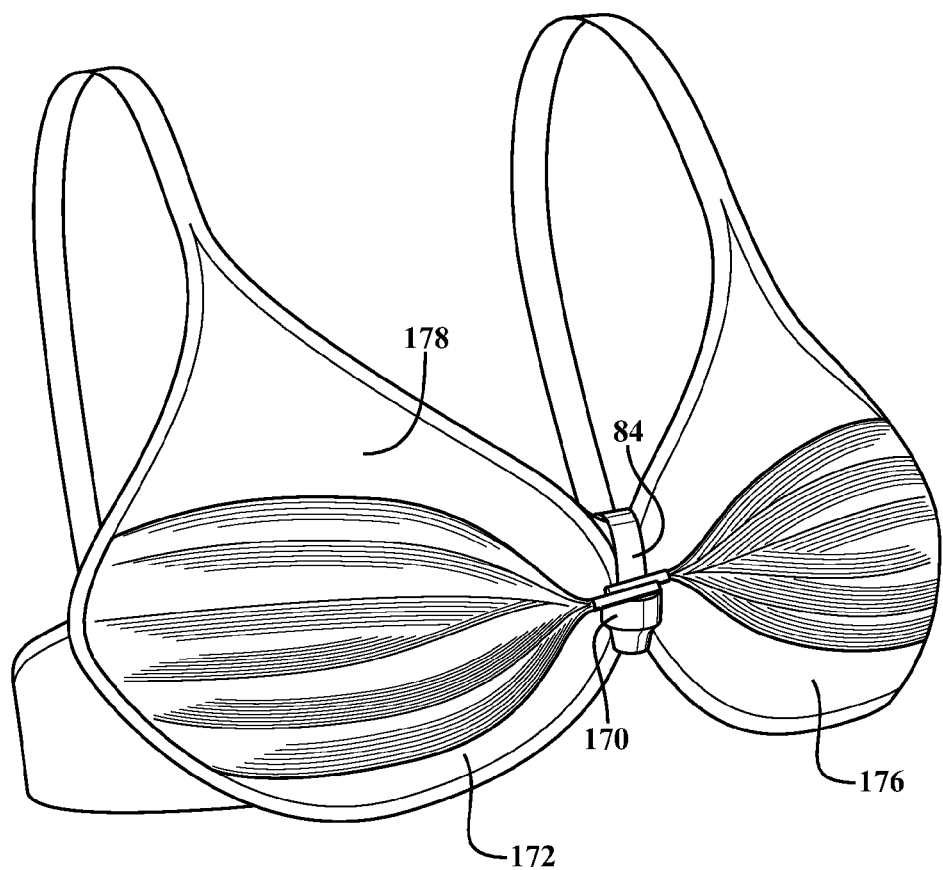
FIG. 33 is a pictorial representations of alternate illuminatable article.

Referring now to FIG. 33, use of the horizontally arranged holder 50 shown in FIG. 26 attached to a circular shaped battery compartment 170 is mounted by means of an attachment member, such as a clip 84, over in a center portion of a bra 172 between the bra cups 174 and 176. The illuminated fabrics 20 have the bound ends 46 removably mountable in the holders 50 and extend in opposite directions over a back material layer 178 of each bra cup 174 and 176. The ends of the fabric 20 spaced from the bound ends 46 may be fanned out over the surface of the cup as shown in FIG. 33 or arranged in any desired decorative pattern. A decorative front panel 180, such as lace, is then attached to the rear surface 178 of the bra cups 174 and 176 to complete the bra construction.

Any of the holders 200, 200¹ and 201 may be mounted on a clothing article, such as a bra, by attaching a spring clip, like clip 84 in FIG. 24, to the holder 200, 200¹ or 201 such as by providing a slot like receiver on the holder to receive one leg 82 of the clip 84.

A laser light therapy apparatus is disclosed which uses a class II, III, or IV laser which produces class I laser output enabling the apparatus to be used by ordinary people, without any training in the use of laser therapy apparatus as is typically required by class II, III or IV lasers which require skilled practitioner training and use.

Although the following description of the laser light therapy apparatus employs a class III laser power source, it will be understood that this is by example only as the laser light power source may be any of a class II, class III or class IV laser light source. It will also be understood that the laser light source may be provided in any wavelength or color, as well as in visible, infrared, or ultraviolet wavelengths.

Referring now to FIG. 34, there is depicted a light therapy apparatus 410 using a laser light generating source 412, a light applicator 414, a control means 460 and a power supply 418. A data storage memory 420 may be coupled to the control means 460 as described hereafter.

The laser light generating source 412 includes a housing 422 with an end coupling 424. At least one laser diode 426, such as a 150 mw-200 mw class III laser diode emitting 650 nm visible red light, is mounted within the housing 422. The laser means emitting various light wave lengths including one of, Blue 405-435 nm for cosmetic applications. Yellow/orange 590 nm for collagen stimulation, red 635-660 nm and infrared 790-830 nm for therapeutic. For specialized tools, a blue light at a wavelength 256 nm can be implemented to sterilize the light applicator coupled to the laser. The laser diode 426 is rated as a class III laser, for example.

The light applicator 414 functions to transform the class III light output of the laser diode 426 in the housing 422 to a class I laser output in the application region 28 of the light applicator 414.

In one aspect, the light applicator 414 can be a woven fiber optic pad sold by Luminex as shown in FIG. 11. The light applicator 414 includes a plurality of individual fiber optic rods or filaments 430 bound at one end by a ferrule 436 adapted to the removably engaged with the coupling 426 on the end of the laser housing 422.

The coupling 426, shown in FIGS. 34D, E, and F includes an end sleeve 440 which is releasably engagable with the end of the laser housing 412 by means of an interlocking projection and recess. A receiver 442 in the form of a hollow cylindrical member extends from the MP3 player 440 and is adapted to releasably and securely receive the ferrule 432 on one end of the light applicator or optical fabric 414. A cap 444 extends from the MP3 player 440 and surrounds a portion of the receiver 442. An end 446 of the cap 444 is spaced at the end of the receiver 442 to allow insertion of the ferrule 432 into the receiver 442.

The open edge of the cap 444 extends below the edge of the receiver 442 as shown in FIG. 34F. The cap 444 prevents direct view of the laser output from the end of the laser housing 412.

When the ferrule 436 is secured within the receiver 442, the fabric or fiber optic rods 414 are bent out of the longitudinal axis of the laser housing 412 at an angle, as shown in FIG. 34F.

The fiber optic rods or filaments 430 are interwoven into a pad-like shape 428 which defines the light application region 428. Due to losses in light intensity, between the coupling 426 light, the ends of the fiber optic rods 430 and the diffuse arrangement of the light output of the pad 414 in the light application region 428, the fiber optic rods 430 thus serve the dual purpose of light transmission and pad reinforcement, the light applied to the patient in the light application region 428 of the light applicator 414 is rated as a class I or IM laser output which is suitable for use by anyone without any training or skill in the use of lasers and can be directly viewed by such persons without protective measures or harmful effects.

The advantage of the light application pad 428 is that it provides a uniform dispersion area of light and not an individual light point or points thereby contributing to the transformation of the class III laser output to a class I laser rating at the light application region on a patient.

It is also possible to provide a woven fiber optic pad which includes two discrete interwoven arrangements of fiber optic rods 430, each separate group of rods being held together by a discrete ferrule 432. Each ferrule 432 may be connected to a light therapy apparatus having a different wavelength laser to selectively or combinationally provide the two distinct laser wavelengths to a patient.

In addition to the light application fiber optic pad 414, the light applicator 414 could also be made of an acrylic plate which is edge illuminated by the fiber optic rods 430 to provide the desired uniform light dispersion over the area of the plate.

The outer surface of the pad 414 facing away from the surface which faces or contacts the patient's body can be provided with an internally reflective surface so as to direct all light energy away from the outer surface toward the patient.

Both the secure fit of the ferrule 432 in the laser housing coupling 424 and the diffuse dispersion of the light energy over a wide area by the light applicator 414 contributes to the class I laser output rating thereby enabling individual patients to use the light therapy apparatus 10 without safety precautions, training, etc.

The control 416 may be a circuit element which is operatively coupled to the laser diode 26 and which controls the activation of the laser diode 426 at a predetermined duty cycle or frequency over a predetermined time interval or number of time interval or intervals. For example, the control 416 may be provided with circuit elements, or software instructions in the case of a central processing unit, which provide duty cycles of 50% and 75% selected by input buttons or touch screen points. The control 416 also applies the duty cycle frequency of 50% or 75% to the laser 426 for a predetermined time interval, such as 15 minutes, and is capable of repeating the time interval of application a selectable number of times over a given longer time interval, such as three times for every four hours, etc.

The power supply 418 can be storage batteries or, preferably, rechargeable storage batteries. The batteries used in the power supply 418 may be recharged separate from the laser apparatus 410 by removing the batteries from the power supply housing or recharged directly within the housing through an internal recharge circuit. In this instance, an external conductor is coupled to an external power supply or outlet to provide 110 VAC power to the control 416 which transforms the power through a recharge circuit to recharge the batteries in the power supply 418.

As the duty cycle programs in the control 460 are essentially frequency signals, the program of each duty cycle application for the duration of a predetermined time may be considered a "tune" as in the same meaning of "tunes" used in widely available MP3 players, such as MP3 player 440 in FIG. 35. The MP3 player 40 includes an internal memory and power supply which is capable of storing the plurality of selectable tunes for frequency outputs. These can be selected through a selector or rotatable wheel 442. A display may also be provided on the MP3 player 440.

As shown in FIG. 35, an MP3 player 450 with a selector wheel 452 and a visible display 454 contains the laser power supply 418 and the control 416 internally within its housing. A connector 456 is formed in the housing 456 of the MP3 player 450. The connector 456 may be a standard USB or 3.5 mm connector coupled to the laser 412 for both powering the laser 412 as well as outputting the frequency "tunes" to control the activation of the laser diode.

That same connector 456 may be used to receive a USB or mini-USB connector 458 which is connected to an external electrical power supply, such as an electrical outlet, for supplying power to an internal recharge circuit within the MP3 player 450 to recharge the battery used within the MP3 player 450.

Referring now to FIG. 6, there is depicted the laser apparatus 412 described above and shown in FIG. 34 connected to a swivel connector 480. The swivel connector 480 carries a 3.5 mm jack 482 for plug in connection to the control 416 or to one of the MP3 players 450 which have a suitably formed 3.5 mm plug.

The swivel connector 480 includes first and second pivotally interconnected sections 84 and 86. The first section 84 carries the 3.5 mm jack 82. The second section 86 is plug in connectible or fixedly mounted to one end of the laser apparatus housing 22.

The swivel sections 84 and 86 may be provided with detents at predetermined angular spacings, such as every 45 or 90 degrees, for example, to provide a secure, fixed mounting of the laser apparatus 412 to the control 416, or to the MP3 player 450 in multiple angular orientations as shown in phantom in FIG. 36.

As shown in FIG. 37, the swivel section 484 can alternately carry a USB connector 496.

It will be understood that the light applicator means 414 may take other forms besides the pad shape shown in FIG. 34. The applicator means 414 may be incorporated into any shaped object or article of clothing, such as a circular sleeve for application about a human limb, a bra, pants, shirt, etc. The light applicator means 414 may also be incorporated into or combined with a limb boot or negative pressure wound dressing 270 shown in FIG. 19. In all cases, however, the light applicator 14 transforms the output light intensity of the laser diode 26 to a low level consistent with a class 1 rated laser for safe application and use by a patient without requiring safety precautions, training or a skilled practitioner to use a laser apparatus 412.

The light applicator means, such as the light applicator pad 414, may also be provided with one or a plurality of distinct laser light output points or locations, rather than emitting laser light over a large light application region 428. The individual points or locations may be arranged in any configuration to provide point directed laser light onto a patient.

Referring now to FIGS. 38-41, there are depicted various aspects of an optical bandage using a light applicator and a light source. The light source may be any of the laser light source 412 described above. Alternately, the light source may be any therapeutic light source, such as various wavelengths of light emitted from light emitting diodes (LED's), a halogen light, etc.

The light applicator may be coupled to conventional bandage or wound dressing materials in either a layered construction or an interwoven construction.

Figure 38:
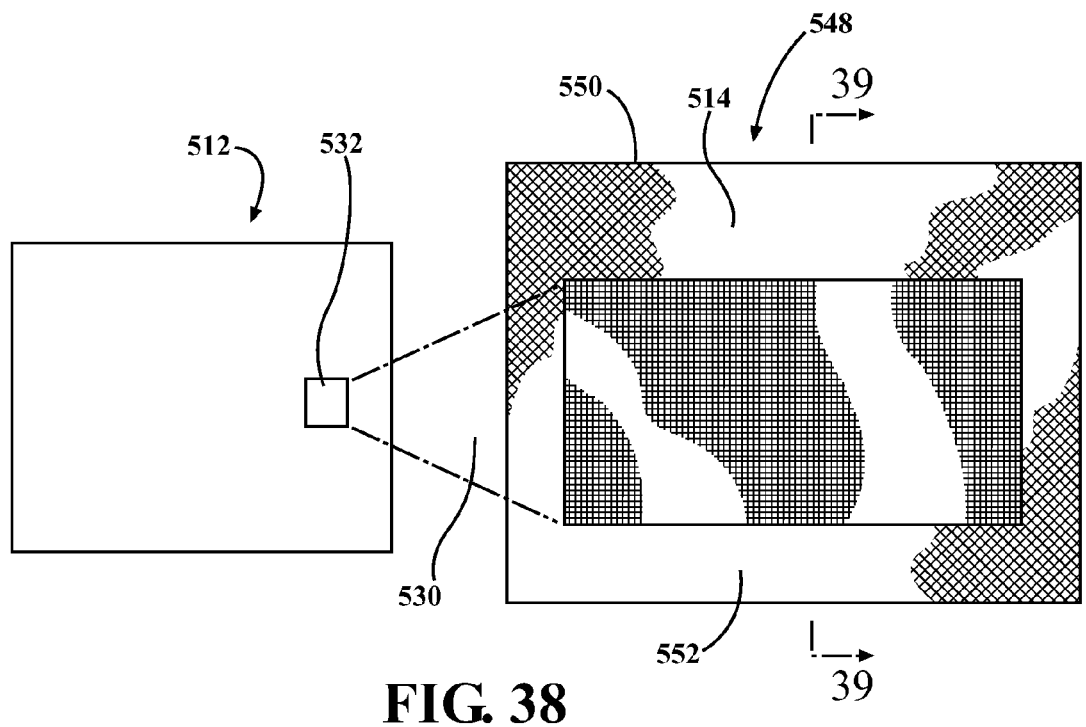
FIG. 38 is a side elevational view of one aspect of an optical bandage coupled to a light source.
Figure 39:
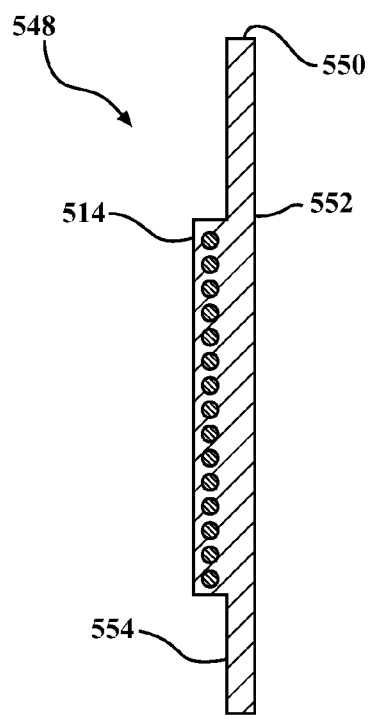
FIG. 39 is a cross sectional view, generally taken along line 39-39 in FIG. 38.

The light applicator 514 shown in FIGS. 38 and 39 may be the light applicator pad 14 made by Luminex, as described above and shown in FIG. 31, which is layered by placing the light applicator pad 14 in contact with one or more layers of a conventional bandage or wound dressing material 550 to form the optical bandage 540. The wound dressing material has a first surface 552 and an opposed second surface 554. The material 550 may have any desired shape, such as square, rectangular, strip form, circular, etc.

The first surface 552 is configured for contact with the patient; while the opposed second surface 554 is configured for contact with the light applicator pad 514. In this manner, the layer 550 prevents contact between the patient's body and the light applicator pad 514.

The dressing layer 550 should be porous to act as a breathable surface when placed on a patient's body, particularly a wound, and light transmissive, such as transparent or slightly translucent, to allow substantially all of the light energy from the light applicator 14 to pass through the layer 550. The layer 550 should also have a degree of flexibility to enable it to be easily and comfortably applied to a patient's body and held on the patient's body by means of a wrap around configuration having one or more layers or using separate adhesive strips or other breathable wrapping materials, such as an Ace bandage.

Figure 40:
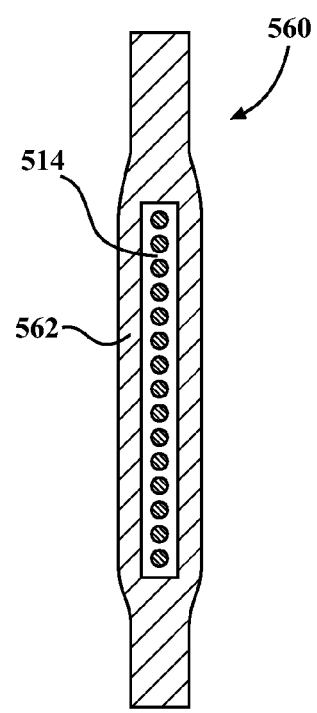
FIG. 40 is a cross sectional view of another aspect of an optical bandage using a layered light applicator.

The optical bandage 560 shown in FIG. 40 has the light applicator pad 514, completely encompassed or sandwiched within an outer layer of bandage or dressing material 565.

The outer layer 562 may be a pad having one or more open ends to allow insertion of the light applicator pad 14 into an interior cavity in the layer 562. Alternately, the outer layer 562 may be formed in an enlarged sheet and then folded over the light applicator 514, with the opposed edges seamed or heat sealed together to form a closed enclosure retaining the light applicator pad 514 therein.

The optical bandage 560 shown in FIG. 40 forms a self contained bandage or dressing which can be easily manipulated, stored and easily applied to any part of a patient's body. Alternately, the optical bandage 560 may be formed as an enlarged sheet for use as a bed pad, therapeutic cloth, or diaper. In this manner, the optical bandage 560 may be wrapped or held onto a patient's body part for light therapy purposes, or may be an entirely separate pad or sheet which contacts a body part.

The layers 550 in the optical bandage 548 and the outer layer 562 in the optical bandage 560 may be constructed of a dry material in order to provide a clean and/or sterile dressing. Alternately, the layers 550 and 562 may be impregnated with medicaments. This provides the synergistic advantage as the light energy from the light applicator 14 pulling the medicaments into the patient's body for expedited healing.

For example, the layers 550 and 562 may be impregnated with colloidal silver amalgamate. Other materials which may be used to impregnate the layers 550 and 552 may be an oil emulsion, hydralonic acid for skin care and scar reduction, as well as various moisturizers, anti-aging compounds, anti-bacterial compounds, etc. For example, the layers 550 and 562 may be formed of an oil emulsion non-adherent dressing sold by Medline, and anti microbial alginate dressing sold under the trademark SILVER CEL by Systagenix Wound Management, Inc., or an Aqua Cel dressing sold by Convalec.

In another aspect, the layers 550 or 562 may be formed of Hydro Fiber sold by Convatec. The Hydrofiber, material is formed with fibers which transitions to a gel-like state when exposed to fluid to absorb and lock in the fluid without significant lateral spread or wicking of the fluid beyond the point of contact of the material with patient's body.

Figure 41:
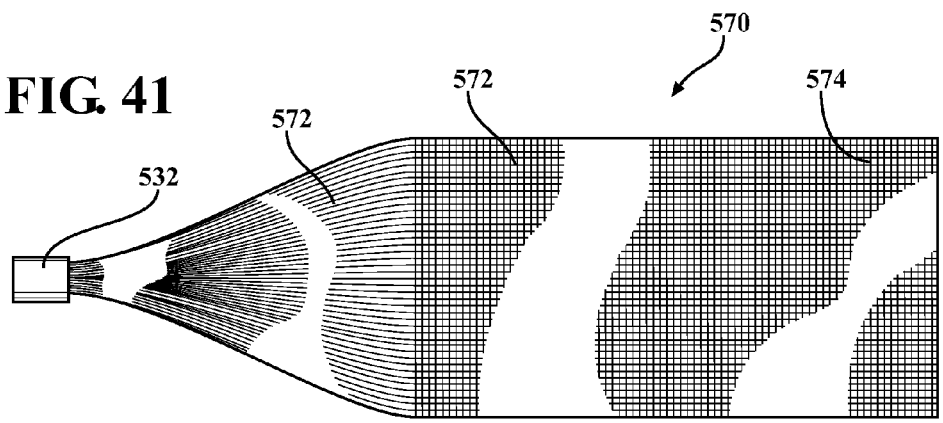
FIG. 41 is an elevational view of another aspect of an optical bandage using an interwoven light applicator.

Referring now to FIG. 41, there is depicted another aspect of an optical bandage 570. In this aspect, light applicator fiber option rods 572 are interwoven with cross fibers 574 to form an interwoven, single piece layer or pad. The interweaving of the light transmissive rods 572 and the fabric fibers 574 can be done according to the textile product described in U.S. Pat. No. 7,234,853 and manufactured by Luminex, S.p.A., Prato, Italy. The fibers 574 and the light transmissive rods 572 may be provided in any desired percentage relationship depending on the particular application. For example, the light transmissive rods 72 may form from ten to sixty percent of the total fabric weight of the optical bandage 570.

The fibers 574 can be made of suitable materials, such as cotton, synthetics, etc., as long the fibers do not interfere with the transmission of light energy from the light transmissive rods 572. Further, the optical bandage 570 can be formed as a porous, breathable weave for use as wound dressings and bandages.

The interwoven bandage 570 has the advantage that the fibers 574 absorb extrudate from the patient; the interwoven light transmissive rods 572 will remain uncovered by the fibers 574 and therefore capable of continually providing light energy to the patient.

Figure 42:
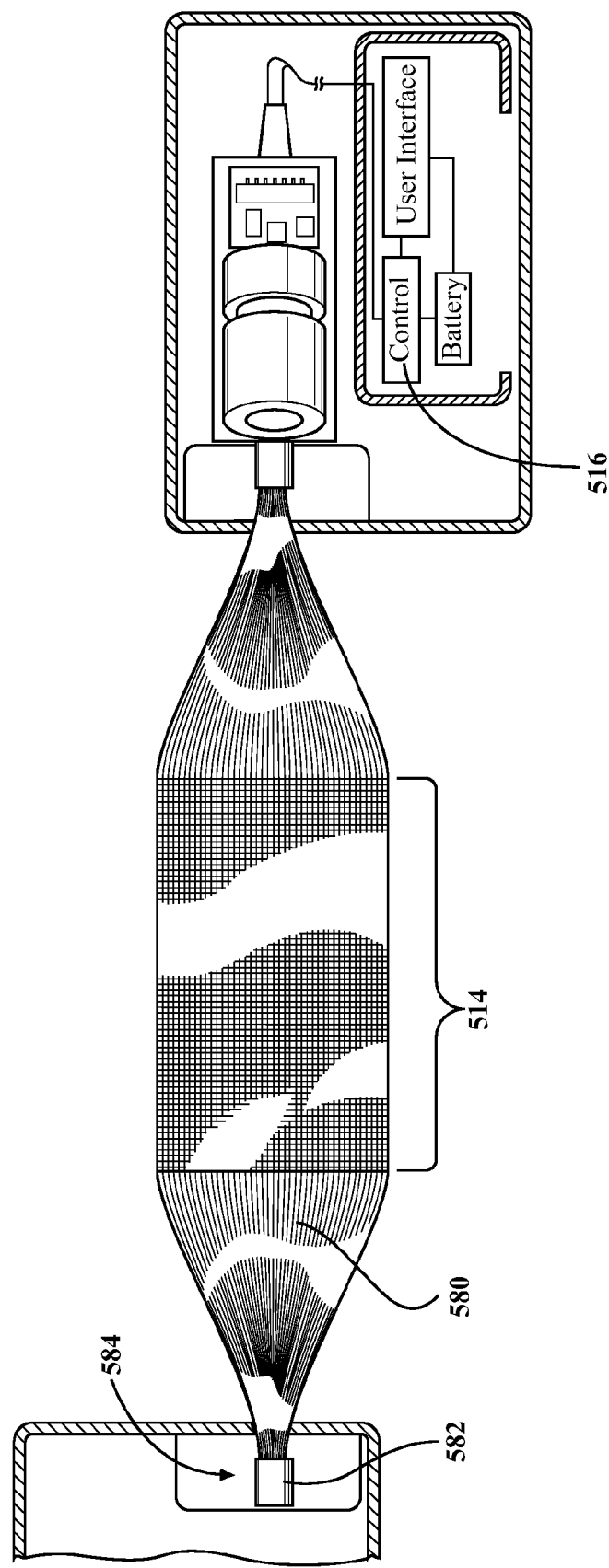
FIG. 42 is an elevational view of an optical bandage with a light intensity sensor.

FIG. 42 depicts an optical bandage using either the light applicator pad 14 or the interwoven fiber and cloth applicator 570, but with a modification in which a percentage, such as 50 percent of the light transmitting or fiber optic fibers 580 extending through the light applicator pad 14 or cloth 570 are continued out of the opposite end of the pad 414 and collected in a separate ferrule 582. The ferrule 582 is mounted in a sensor 584, such as, for example, an SO₂ oxygen sensor, etc. The fibers 580 and ferrule 582 could also extend out of the same end of the pad 14 as the ferrule 32.

The dual fiber optic bundles shown in FIG. 42 function to direct light from the light source through the applicator 414 onto a portion of a patient's body, such as a wound and, at the same time, collect reflected light through the fiber optic rods 580 and direct the reflected light to the sensor 584 for analysis.

This arrangement can be used to detect the healing affect of the light applied to the patient's body.

The interwoven pad 570 shown in FIG. 42 can be used separately from its described application as an optical bandage, as a high, bright illumination for articles of clothing or equipment. For example, a 50/50 ratio of fiber optic rods 572 and cloth fibers 574 can be applied to articles of clothing, such as emergency and warning clothing, and/or pads or sheets which can be applied onto equipment for emergency warning purposes.

Figure 43:
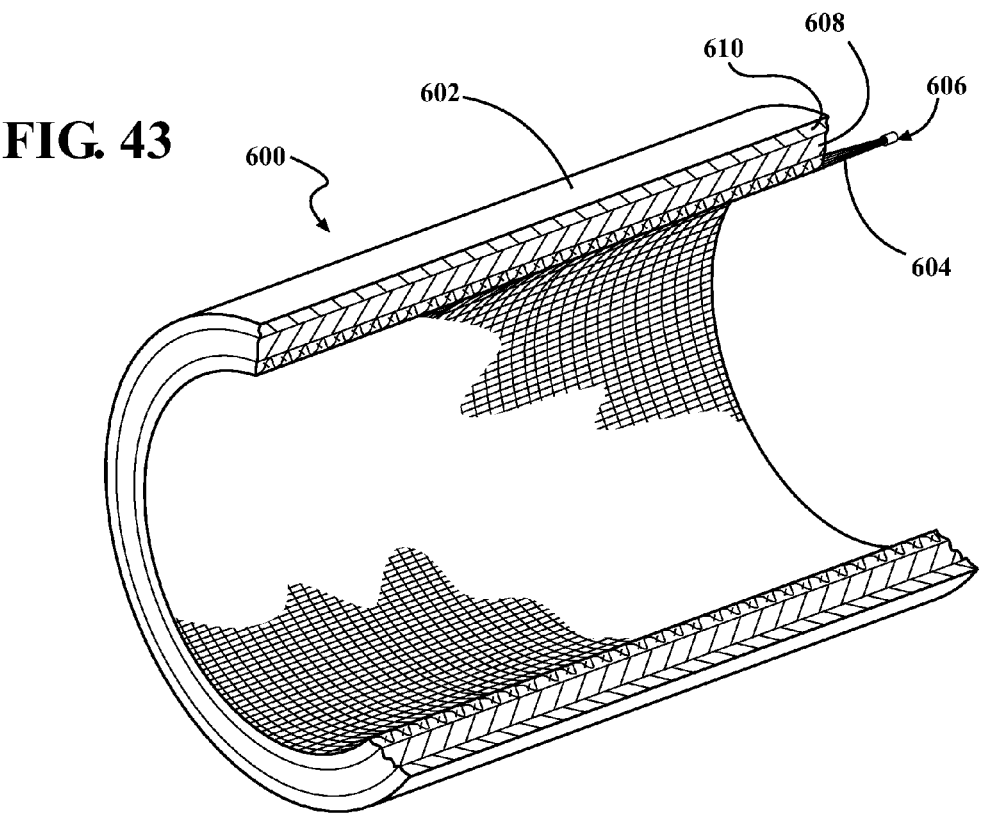
FIG. 43 is a perspective cross-sectional view of an optical cast.

FIG. 43 depicts an optical cast 600 for use in speeding the healing of broken bones. The cast 600 includes an inner layer 602 of an interwoven fiber optic/fiber sheet, as described above and shown in FIG. 43. The fabric and the layer 602 may be woven cotton gauze in addition to the fiber optic fibers or rods 604. The ends of the rods 604 extend outward from one end of the layer 602 and are secured by a ferrule 606 for connection to a light source as in previous optical bandages described above.

To complete the cast 600, a shock absorbent layer 608, typically formed of cotton is wrapped around the layer 602. Finally, an outer layer 610 formed of fiberglass plaster is formed around the layer 608 to complete the cast 600.

In addition to immobilizing the broken bone, cast 600 also provides light therapy through the fiber optic rods 604 in the inner layer 602 to increase healing.

It should be noted that the layer 602 can be formed of several concentric wraps of the interwoven cloth and fiber optic rods for increased light radiation and light intensity.

The light source which can be applied to the fiber optic rods 604 can be either visible laser or LED light to enhance peeling of the skin and wounds and an infrared light source for healing of bone, meniscus and bone marrow.

Appropriate resonate frequency adjustments for tissue type can be made during the application of light energy to the fiber optic rods 602 as well as through the entire healing process.

The light therapy apparatus is indicated for the temporary relief of minor muscle and joint pain, arthritis and muscle spasm, relieving stiffness, promoting relaxation of muscle tissue, and to temporarily increase local blood circulation.

Figure 19A:
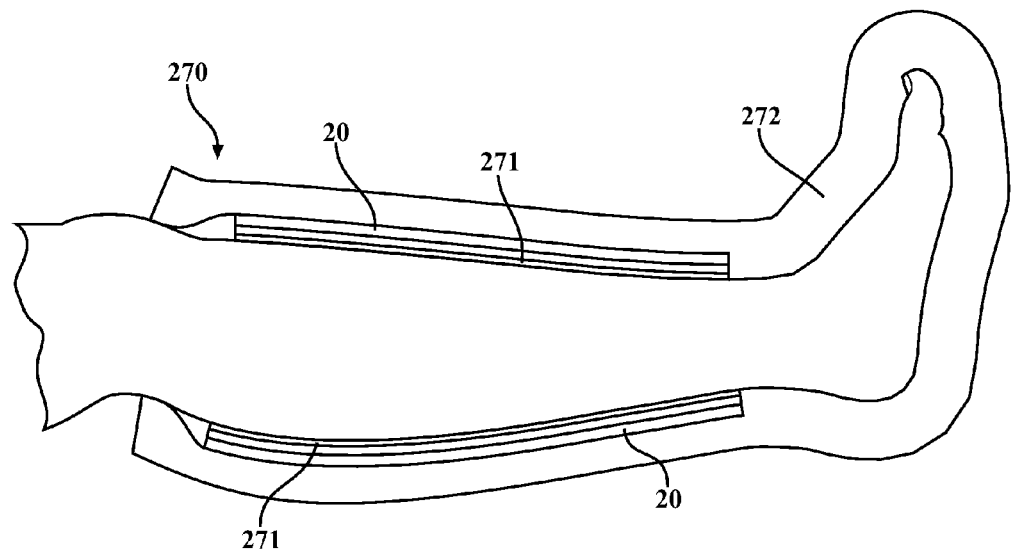
FIG. 19 is a side elevational view of a negative pressure wound device using an optical fabric.
Figure 19B:
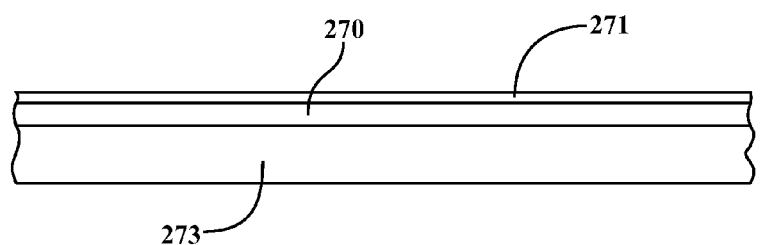
Figure 20:
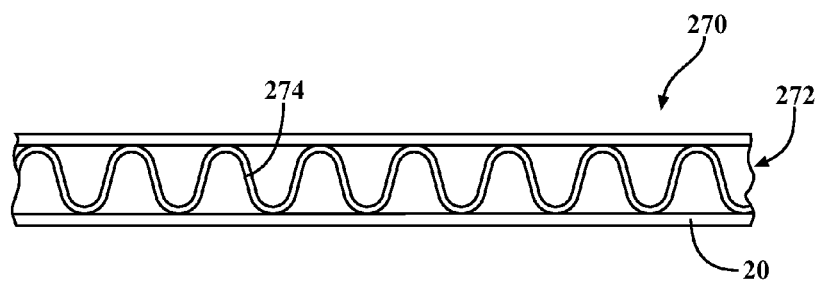
FIG. 20 is a cross sectional view showing the integration of an illuminated fabric layer in the device shown in FIG. 19.

The optical fabric described in various aspects above with one or more of the above described light source and power source holders, such as a holder 200, may also be advantageously employed to provide light therapy in other medical applications, as shown in FIGS. 19 and 20.

FIG. 19A depicts in pictorial form a wound dressing boot, such as a boot sold by Rooke, or a negative pressure device. Such wound dressings or negative pressure devices include an outer layer of porous material, such as cotton, cellulose, foam, etc. In one aspect of the present illuminatable article, a fiber optic sheet 20 is interposed between the outer porous of the wound dressings or negative pressure devices and a thin porous layer 271 disposed adjacent to the patient's body. The fiber optic sheet 270 provides light therapy to the adjacent portion of the patient's skin or wound while still allowing the wound to discharge to flow through the fiber optic sheet 20 into or through the porous outer layer 272.

The present illuminatable article may also be incorporated into a bed pad or bed sheet as generally shown in FIG. 19B. In the case of bed pad, such as an 18'×18' inch bed pad, the underlying layer of material typically formed of cotton, cellulose or other sterile materials usable in hospitals, etc., forms a support for a fiber optic panel or sheet 270. An outer layer of porous material 271 which acts as protective layer in contact with the patient's skin is interposed over the fiber optic panel 270.

The same construction shown in FIG. 19B applies equally to a full sized bed sheet. In the case of a full sized bed sheet, multiple light sources may be connected to sections of fiber optic rods extending through the bed sheet.

The fiber optic panel 270 may be formed as a separate layer sandwiched between the outer porous layer 271 and the underlying support layer 273. Alternately, the fiber optic panel 270 may be interwoven with the outer layer 271 and/or the underlying support layer 273.

Numerous companies, such as Convatec, Smith&Nephew, KCl and others, sell negative pressure wound devices. Such devices are designed for applying a vacuum to a boot or enclosure mounted over a user's wound, such as a leg wound, to draw wound discharge through the boot or enclosure to promote wound healing. Such negative pressure devices have proven effective at increasing patient comfort and healing of wounds. It is believed that further improvements can be obtained by applying light therapy in conjunction with the negative pressure aspect of such devices.

Generally, such negative pressure devices use a layer 272 of porous material which allows the wound discharge to be drawn by a vacuum from the patient's skin through the layer 272 along a discharge path. As shown in FIG. 20, one or more optical fabric sheets 20, as described above, can be mounted in the porous negative pressure layer 272 or layers, such as between the inner and outer surfaces in internal corrugations 274 of one negative pressure device shown by example only in FIG. 20. Since the optical fabric sheet 20 described above is also porous, the wound discharge can be drawn through the fabric 20 by the negative vacuum pressure in the normal manner. However, it has been shown that the application of light at predetermined frequencies and at predetermined rates has a therapeutic effect at increasing the blood circulation which can further promote wound healing.

As negative pressure wound devices are formed in various buildups of materials, such as foam, wrapped layers, laminated or extruded layers; the optical fabric layer 20 shown in FIG. 21 can be applied during a foaming process, in-between the various layers as the layers are wrapped around a form to form the negative pressure device, between two layers which are subsequently laminated together, or between two extruded layers of material. These processes securely attach the optical fabric layer 20 within the negative pressure layers 272 while retaining the desired porosity of the negative pressure device and the optical fabric layer 20.

What is claimed is:

1. An illuminatable article comprises:
laser means for emitting at least one laser beam of laser light having a light intensity greater than a class I laser rating;
a power supply operatively connected to the laser means;
a control, operatively connected to the power supply and the laser means, for controlling the laser means to emit laser light for a predetermined period of time; and
means, optically coupled to the laser means, and including an optical light transmission media for diffusing the intensity of the laser light generated by the laser means to an intensity no greater than the output of a class I rated laser in a light application region.

2. The illuminatable article of claim 1 wherein the laser means is one of a class III and a class IV rated laser.

3. The illuminatable article of claim 1 wherein the diffusing means comprises:
the optical light transmission media optically coupled at one end to the laser means; and
the optical transmission media mounted in an enlarged pad for diffusing the laser light over the pad.

4. The illuminatable article of claim 3 wherein the control comprises:
a circuit element activating a laser means for a predetermined period of time and predetermined period of times over a longer predetermined time interval.

5. The illuminatable article of claim 4 wherein:
the control includes a first frequency output activating the laser means at a first duty cycle over a predetermined time interval.

6. The illuminatable article of claim 4 wherein:
the control has a plurality of distinct frequency outputs.

7. The illuminatable article of claim 5 wherein:
the first frequency output duty cycle and the predetermined time interval defines an audio tune.

8. The illuminatable article of claim 4 wherein:
the control, the laser means and the power supply are coupled together as a unitary device.

9. The illuminatable article of claim 1 comprising:
the control capable of outputting a plurality of selectable distinct audio tunes for therapeutic purposes.

10. The illuminatable article of claim 9 wherein:
the control is capable of electronically playing frequencies.

11. The illuminatable article of claim 1 wherein:
the laser means emits light wave lengths including one of Blue 405-435 nm for cosmetic applications, Yellow/orange 590 nm for collagen stimulation, red 635-660 nm, and infrared 790-830 nm for therapeutic use.

12. The illuminatable article of claim 1 wherein:
the laser means emitting a blue light at a wavelength 256 nm to sterilize a fabric sheet coupled to the laser means.

13. A light therapy apparatus comprising:
a housing carrying a power supply;
a laser light source operatively coupled to the power supply;
a control, operatively coupled to the power supply and the laser light source for controlling the laser light source to emit laser light;
an optical transmission media having an end coupled to the housing in light transmission relationship with the laser light source, for transmitting laser light from the laser light source through the optical transmission media; and
a cap extended from an end of the housing receiving the end of the optical transmission media, the cap deflecting the optical transmission media out of a longitudinal axis between the laser light source and the end of the optical transmission media to minimize direct user eye visibility of the laser light source in the housing.

14. The light therapy apparatus of claim 13 wherein:
the end of the optical transmission media is removably coupled to the housing.

15. The light therapy apparatus of claim 13 further comprising:
the cap partially encircling the end of the optical transmission media coupled to the housing.

* * * * *